US008814807B2

(12) United States Patent
Hulvershorn et al.

(10) Patent No.: US 8,814,807 B2
(45) Date of Patent: *Aug. 26, 2014

(54) SPINAL CANAL ACCESS AND PROBE POSITIONING, DEVICES AND METHODS

(75) Inventors: Justin Hulvershorn, Seattle, WA (US); Karl Schmidt, Seattle, WA (US); Douglas Swartz, Seattle, WA (US)

(73) Assignee: Mirador Biomedical, Seattle, WA (US)

( * ) Notice: Subject to any disclaimer, the term of this patent is extended or adjusted under 35 U.S.C. 154(b) by 61 days.

This patent is subject to a terminal disclaimer.

(21) Appl. No.: 12/806,747

(22) Filed: Aug. 19, 2010

(65) Prior Publication Data

US 2011/0054353 A1    Mar. 3, 2011

Related U.S. Application Data

(60) Provisional application No. 61/235,004, filed on Aug. 19, 2009, provisional application No. 61/300,794, filed on Feb. 2, 2010.

(51) Int. Cl.
| | | |
|---|---|---|
| *A61B 5/103* | (2006.01) | |
| *A61B 5/00* | (2006.01) | |
| *A61B 5/03* | (2006.01) | |
| *A61M 25/06* | (2006.01) | |
| *A61B 17/34* | (2006.01) | |
| *A61B 19/00* | (2006.01) | |

(52) U.S. Cl.
CPC .......... *A61M 25/0693* (2013.01); *A61B 5/4821* (2013.01); *A61B 5/032* (2013.01); *A61M 25/06* (2013.01); *A61B 5/036* (2013.01); *A61B 17/3401* (2013.01); *A61B 2019/465* (2013.01)
USPC .......................................... 600/561; 604/272

(58) Field of Classification Search
CPC ...................................... A61B 5/4896
USPC ............................... 600/561, 573
See application file for complete search history.

(56) References Cited

U.S. PATENT DOCUMENTS 4,648,406 A * 3/1987 Miller ........................ 600/487
4,801,293 A * 1/1989 Jackson ...................... 604/505
(Continued)

FOREIGN PATENT DOCUMENTS

EP         0 538 259       4/1993
KR       20020073824    *  9/2002    ............. A61B 5/103
(Continued)

OTHER PUBLICATIONS

Don et al. "A Study of Correlation between Epidural and CSF Pressure," The Journal of Korean Society of Anesthesiologists: vol. 23, No. 2, 1990.*

(Continued)

*Primary Examiner* — Sean Dougherty
*Assistant Examiner* — Michael C Stout
(74) *Attorney, Agent, or Firm* — Wilson Sonsini Goodrich & Rosati

(57) ABSTRACT

Methods and devices for detecting positioning of a probe in a tissue of a patient. A method can include providing a detection device; advancing a device coupled probe through the tissue of the patient and toward the patient's spinal canal; detecting a change in pressure about the distal portion of the coupled probe during advancing, where the detected pressure change indicates probe positioning in the patient's spinal canal; outputting the detected pressure change or indication of probe positioning to a visual display.

34 Claims, 14 Drawing Sheets

(56) References Cited

U.S. PATENT DOCUMENTS

| | | | |
|---|---|---|---|
| 5,205,828 A | | 4/1993 | Kedem |
| 5,267,971 A | | 12/1993 | Brimhall |
| 5,314,410 A | | 5/1994 | Marks |
| 5,526,820 A | * | 6/1996 | Khoury .......................... 600/561 |
| 5,575,789 A | * | 11/1996 | Bell et al. ......................... 606/42 |
| 5,711,302 A | * | 1/1998 | Lampropoulos et al. ..... 600/485 |
| 5,865,764 A | * | 2/1999 | Moorhead ..................... 600/561 |
| 5,871,470 A | * | 2/1999 | McWha ........................ 604/158 |
| 5,902,273 A | | 5/1999 | Yang et al. |
| 5,954,701 A | * | 9/1999 | Matalon ......................... 604/272 |
| 6,623,429 B2 | * | 9/2003 | Percival et al. ................ 600/399 |
| 7,585,280 B2 | * | 9/2009 | Wilson et al. .................. 600/561 |
| 7,618,409 B2 | * | 11/2009 | Hochman ...................... 604/506 |
| 7,896,833 B2 | * | 3/2011 | Hochman ........................ 604/65 |
| 7,922,689 B2 | * | 4/2011 | Lechner .......................... 604/66 |
| 7,955,301 B1 | * | 6/2011 | Mckay .......................... 604/121 |
| 8,142,365 B2 | * | 3/2012 | Miller ........................... 600/566 |
| 2002/0010390 A1 | * | 1/2002 | Guice et al. ................... 600/300 |
| 2003/0199909 A1 | * | 10/2003 | Boecker et al. ................ 606/181 |
| 2004/0010204 A1 | * | 1/2004 | Weber et al. ................... 600/547 |
| 2004/0024358 A1 | * | 2/2004 | Meythaler et al. ............. 604/113 |
| 2004/0098020 A1 | | 5/2004 | Nardeo |
| 2004/0215080 A1 | * | 10/2004 | Lechner .......................... 600/463 |
| 2005/0070458 A1 | * | 3/2005 | John ............................ 514/1 |
| 2005/0148940 A1 | * | 7/2005 | Miller ........................... 604/187 |
| 2006/0036164 A1 | | 2/2006 | Wilson et al. |
| 2006/0122555 A1 | * | 6/2006 | Hochman ........................ 604/67 |
| 2006/0135882 A1 | * | 6/2006 | Bleich ........................... 600/546 |
| 2006/0149161 A1 | * | 7/2006 | Wilson et al. .................. 600/561 |
| 2006/0195043 A1 | * | 8/2006 | Rutherford et al. ........... 600/561 |
| 2007/0038129 A1 | * | 2/2007 | Kishimoto et al. ............. 600/485 |
| 2007/0123888 A1 | * | 5/2007 | Bleich et al. .................... 606/79 |
| 2007/0255220 A1 | * | 11/2007 | King et al. ............... 604/168.01 |
| 2008/0097287 A1 | * | 4/2008 | Nelson et al. ................... 604/65 |
| 2008/0147094 A1 | * | 6/2008 | Bittenson ....................... 606/144 |
| 2008/0154188 A1 | * | 6/2008 | Hochman ....................... 604/67 |
| 2008/0200789 A1 | | 8/2008 | Brister et al. |
| 2009/0005675 A1 | | 1/2009 | Grunwald et al. |
| 2009/0005703 A1 | * | 1/2009 | Fasciano ........................ 600/561 |
| 2009/0131832 A1 | * | 5/2009 | Sacristan Rock et al. .... 600/587 |
| 2009/0157044 A1 | * | 6/2009 | Liyanagama et al. ......... 604/512 |
| 2009/0204119 A1 | * | 8/2009 | Bleich et al. .................... 606/79 |
| 2009/0240205 A1 | * | 9/2009 | Wen ............................. 604/173 |
| 2009/0270759 A1 | * | 10/2009 | Wilson et al. .................. 600/561 |
| 2010/0069851 A1 | * | 3/2010 | Vad et al. ....................... 604/240 |
| 2010/0094143 A1 | * | 4/2010 | Mahapatra et al. ............ 600/486 |
| 2011/0004159 A1 | * | 1/2011 | Nelson et al. .................. 604/151 |
| 2011/0046477 A1 | | 2/2011 | Hulvershorn et al. |
| 2011/0060229 A1 | | 3/2011 | Hulvershorn et al. |
| 2011/0125107 A1 | * | 5/2011 | Slocum et al. ................. 604/272 |
| 2011/0130758 A9 | * | 6/2011 | Bleich et al. .................... 606/79 |
| 2011/0224623 A1 | * | 9/2011 | Velez Rivera ................. 604/239 |
| 2011/0298628 A1 | * | 12/2011 | Vad et al. ....................... 340/665 |

FOREIGN PATENT DOCUMENTS

| | | | | |
|---|---|---|---|---|
| KR | 20020073824 A | * | 9/2002 | ............. A61M 5/46 |
| WO | WO 03/000146 A1 | | 1/2003 | |

OTHER PUBLICATIONS

Usubiaga et al. "Effect of Saline Injections on Epidural and Subarachnoid Space Pressrues and Relation to Postspinal Anesthesia Headache," Anesthesia and Analgesia Current Researches vol. 46, No. 3, May-Jun. 1976.*

International search report and written opinion dated Oct. 15, 2010 for PCT/US2010/002305.

Office action dated Mar. 8, 2013 for U.S. Appl. No. 12/806,809.
Office action dated May 7, 2013 for U.S. Appl. No. 12/806,798.
Office action dated Sep. 6, 2013 for U.S. Appl. No. 12/806,809.
Office action dated Nov. 6, 2013 for U.S. Appl. No. 12/806,798.
Office action dated Nov. 19, 2012 for U.S. Appl. No. 12/806,798.

* cited by examiner

SPINAL CANAL ACCESS AND PROBE POSITIONING, DEVICES AND METHODS

CROSS-REFERENCE TO RELATED APPLICATION

The present invention claims the benefit of priority under 35 U.S.C. §119(e) of U.S. Provisional Application No. 61/235,004, filed Aug. 19, 2009 and U.S. Provisional Application No. 61/300,794, filed Feb. 2, 2010, the entire contents of which are herein incorporated by reference.

The present application is related to U.S. application Ser. No. 12/806,809, filed Aug. 19, 2010, and U.S. application Ser. No. 12/806,798, filed Aug. 19, 2010, both of which are being filed concurrently herewith, the full disclosures of which are herein incorporated by reference.

BACKGROUND OF THE INVENTION

The present disclosure relates generally to systems, methods, and devices for facilitating access to a target anatomical site. More specifically, the present invention provides methods and structures for detecting or facilitating positioning of a probe (e.g. a needle) in the spinal canal of a patient.

A number of medical procedures involve gaining probe access to a patient's spinal canal. Accurately or reliably determining entry or positioning of a medical instrument in the spinal canal is often crucial for optimal delivery of care.

For instance, delivery of epidural anesthesia, a type of anesthesia commonly used in childbirth, involves the insertion of a catheter into the epidural space. To introduce the catheter, a special epidural needle is advanced through the back and into the epidural space; the catheter is then inserted through the needle and into the epidural space. During its passage into the body, the needle passes through skin and soft tissue before entering a tough ligament. The epidural space is just beyond the ligament. The needle must be advanced far enough to reach the epidural space, while advancing too distally should be avoided. If the needle is put in too far, it will pass through the epidural space and puncture a thin layer of tissue (the dura), entering the subarachnoid space and causing a cerebrospinal fluid (CSF) leak.

Accurate positioning of a probe or catheter in the epidural space is a process requiring a degree of precision. Most doctors identify the epidural space using a "loss of resistance" technique, in which the epidural needle is attached to a "loss of resistance" syringe having a plunger that moves back and forth with very little resistance. The needle and syringe are slowly advanced into the patient's back while the plunger is occasionally depressed to test for a "loss-of-resistance." If the needle is in the tough ligament located between the skin and the epidural space, the plunger will not depress easily. If the needle is in the epidural space, however, the plunger will depress more easily. Once the needle is in the epidural space, an epidural catheter is inserted through the needle and into the epidural space. The catheter is then used to deliver anesthesia or other drugs. Sometimes the drug is injected directly into the epidural space through a needle and a catheter is not inserted.

Unfortunately, complications due to faulty positioning or placement of the probe or catheter are not uncommon during epidural procedures. One of the most frequent complications occurs when the epidural needle is accidentally inserted past the epidural space and through the dura, resulting in a cerebrospinal fluid (CSF) leak. Following accidental dural puncture, patients have a greater than 50% chance of developing a post-dural puncture headache (PDPH) resulting from CSF loss. These headaches are often severe and associated with nausea and vomiting, vision and hearing changes, low back pain, dizziness, and cranial nerve palsies. Most of these headaches go away in about a week, but in some instances can last for months or years. Additionally, if left untreated, the headaches can predispose to subdural hematoma and possibly death.

Another common error during epidural anesthesia occurs when a catheter is introduced in an area other than the epidural space, like the surrounding muscles. This error happens because, due to tissue structure differences, these areas can give a false "loss of resistance" upon epidural needle entry. Unfortunately, it is difficult and time consuming to identify misplaced catheters. The current most reliable practice for verifying that a catheter is correctly placed in the epidural space is an injection of local anesthetic and subsequent verification of drug effect. The drug will not take effect if the catheter is not in the epidural space, and since peak effect of correctly delivered drug can take up to 20 minutes, verification by this method can be time consuming. Such a delay can be impractical for a patient in severe pain, and may in fact be dangerous for a woman in need of an urgent caesarean section. In addition to prolonging pain relief, such misplacement necessitates additional procedures, such as additional attempt at epidural anesthesia or even emergency general anesthesia.

Both problems, puncturing the dura and putting the catheter in the wrong place, result because the "loss-of-resistance" technique is simply not particularly sensitive. Further, there is a lack of a suitable alternative that does not involve impractical complexity.

Lumbar puncture is another medical procedure requiring access to the spinal cavity. During a lumbar puncture (or spinal tap) a needle is inserted through a patient's back and into the subarachnoid space to measure the intracranial pressure ("opening pressure") and to collect a sample of cerebrospinal fluid (CSF) for lab analysis. A lumbar puncture is the most reliable method to diagnose meningitis, a life-threatening but highly treatable infection characterized by high fevers, headache, a stiff neck, and elevated CSF pressure. Infants commonly require lumbar puncture as a part of the routine workup for fever without a source, as they have a much higher risk of meningitis than adults and do not reliably show external signs of meningitis, like a stiff neck. Lumbar punctures are also performed to diagnose subarachnoid hemorrhage, hydrocephalus, and idiopathic intracranial hypertension, and to inject medications into the cerebrospinal fluid, particularly spinal anesthetics and chemotherapeutics.

Like epidural procedures, gaining access to the spinal cavity for a lumbar puncture typically relies on the physician's senses of touch or feel. To perform a lumbar puncture, the physician slowly advances a needle into the back until he feels a tactile "pop", stopping needle advancement occasionally to look for return of CSF through the end of the needle in case the pop isn't noticed. The "pop" signals the passage of the needle through a tough membrane called the dura and into the subarachnoid (CSF) space. Unfortunately, the "pop" is not as noticeable in some adult patients as well as in infants generally. Additionally, often the only way to tell when the needle is in the right place is by looking for the return of CSF through the back of the needle. The CSF may take tens of seconds to make its way out the end of the needle, and the physician may have to reposition the needle multiple times before seeing CSF return through the needle, making the procedure very time consuming and uncomfortable for the patient. If the physician advances the spinal needle too far, the needle can damage the blood vessels at the distal side of the CSF space and cause what is known as a "bloody tap" that contaminates the CSF sample and frequently leads to additional procedures. Unfortunately, nearly 20% of pediatric lumbar punctures result in a "bloody tap", in part because the physicians do not have a good indication of when the needle has entered the correct space.

Once the needle is in the CSF space, the physician can measure the CSF opening pressure. Measurement of CSF pressure has long been recommended as part of the lumbar puncture procedure, and is typically accomplished using a liquid column hydrostatic manometer. A liquid column hydrostatic manometer only allows pressure measurement once CSF is obtained, because the height of the column of CSF flowing out of the needle and filling the manometer tube is used to determine the pressure. The manometer is connected to the end of the LP needle directly or via a three-way stopcock. An assistant is typically required to hold the top end of the tube. It can be difficult to perform this measurement for a number of reasons, including the following: potential for attachment and removal of the apparatus and patient movement to dislodge the needle; relatively long time (e.g., several minutes) to acquire a reading; potential for inaccuracy from air bubbles; loss of CSF increasing post-dural puncture headache frequency. Because of these problems, CSF pressure is often not measured during lumbar puncture in children.

Accordingly, improved methods and structures are needed for facilitation of probe access and/or positioning in a spinal canal of a patient, and could significantly improve efficiency and reduce complications associated with many medical procedures such as lumbar punctures and epidural access procedures.

BRIEF SUMMARY OF THE INVENTION

The present disclosure relates generally to systems, methods, and devices for facilitating access to a target anatomical site. More specifically, aspects of the present disclosure relate to methods and structures for detecting or facilitating positioning of a probe (e.g. a needle) in the spinal canal of a patient, including probe positioning, monitoring and the like during medical procedures such as lumbar puncture and access to the epidural space.

In one aspect, the present invention provides methods and structures for positioning, detecting or monitoring a probe for disposal in a spinal canal of a patient. A method can include providing a detection device as described herein. The device can be advanced distally such that the tip or a distal portion of a coupled probe advances through the tissue of the patient and toward the patient's spinal canal. The method further includes detecting a change in pressure about the distal portion of the coupled probe during advancing, where the detected pressure change indicates probe positioning in the patient's spinal canal. The detected pressure change and indication of probe positioning is output, for example, as a reporting signal to the visual display. The user may change or alter advancement of the probe in response to the detected pressure change.

In an embodiment, a detection device includes a housing having a generally proximal portion and a distal portion, the distal portion may be coupled to a probe (e.g. a needle) during use. A device further includes a pressure sensing system at least partially carried by the housing and an output unit carried by the housing. The pressure sensing system includes a processor or processing unit coupled with a pressure sensor so as to receive signal from the pressure sensor and determine a pressure value of an environment about a distal portion of the coupled probe. The output unit is coupled to the pressure sensing system so as to receive a pressure value signal and output to the visual display a reporting signal indicating the determined pressure value and/or positioning of the probe in the tissue of the patient.

Devices and methods include monitoring or detecting positioning of a probe in a spinal canal of a patient, including in conjunction with a lumbar puncture procedure or epidural access procedure. In one embodiment of an epidural access procedure, a device is advanced toward the patient's spinal canal such that the coupled probe enters into the epidural space of the patient's spinal canal. A change of pressure can be detected and indicates entry into the epidural space, which can be output to the device display signaling the user to maintain or alter device positioning, or discontinue advancement. Detecting a change in pressure may include detecting an increase or decrease in pressure, or detecting a waveform pressure pattern characteristic of the patient's epidural space, or combination thereof. An epidural access procedure can further include introduction of an epidural catheter and delivery of anesthesia.

In an embodiment including a lumbar puncture procedure, a coupled probe of a device is advanced toward the patient's spinal canal such that the probe enters into the subarachnoid space of the spinal canal and is in contact with the CSF. Entry into the CSF is indicated by a change in pressure, such as an increase, decrease, or detection of a waveform pressure pattern, or a combination thereof. The method can additionally include further detection or analysis of fluid flowed toward the device, for verification or confirmation of CSF entry. For example, CSF fluid can be flowed back proximally through a positioned needle, in some cases into a coupled device, e.g., out an opening or port of the device, for analysis, visualization, and/or collection. Methods can additionally or alternatively include monitoring of probe positioning in the spinal canal (e.g., epidural space or CSF).

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

The present invention provides methods and structures for detecting and/or facilitating positioning of a probe in the spinal canal of a patient, including probe positioning, monitoring and the like during a spinal canal access procedure, such as a lumbar puncture or epidural access procedure.

Figure 1A:
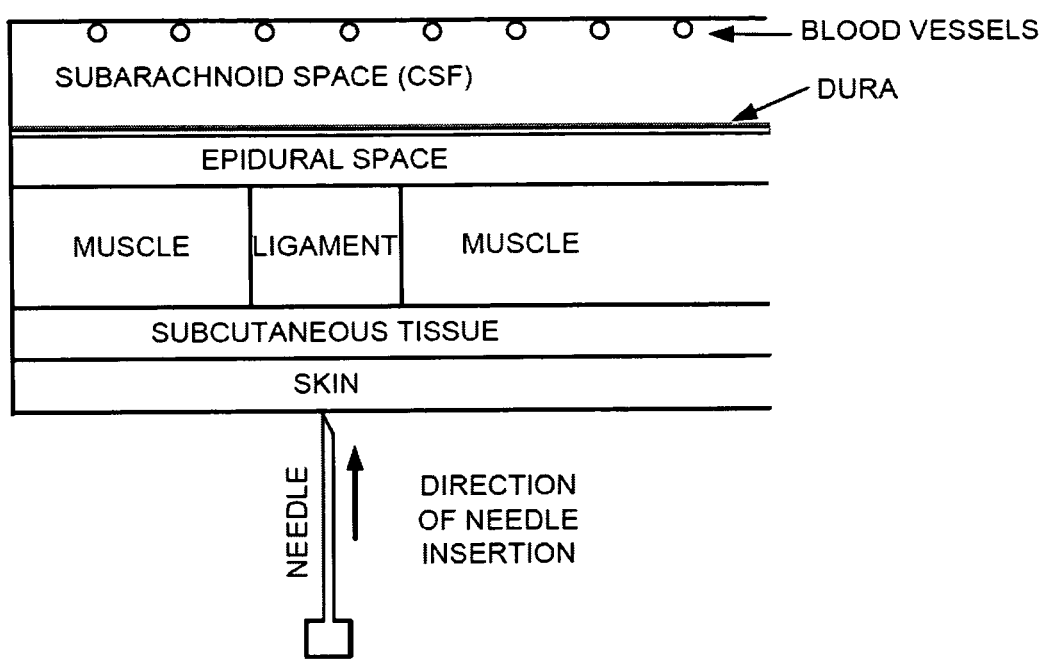
FIG. 1A illustrates needle insertion and anatomical features in the vicinity of a patient's spine.
Figure 1B:
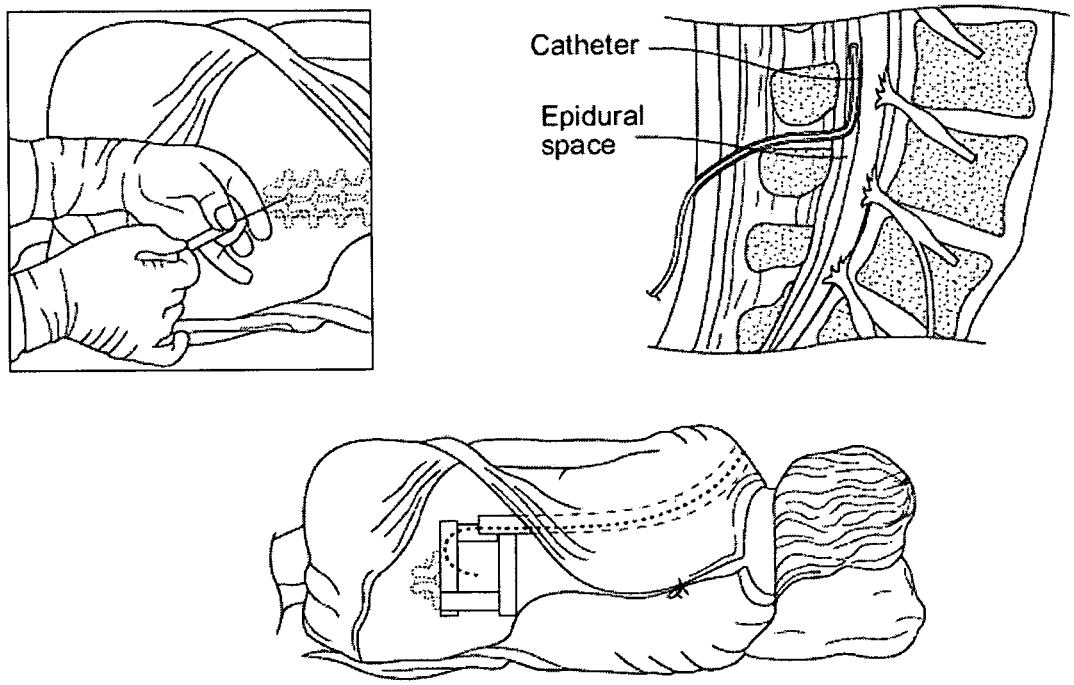
FIG. 1B is an exemplary schematic showing a typical approach for epidural access and delivery of epidural anesthesia.
Figure 1C:
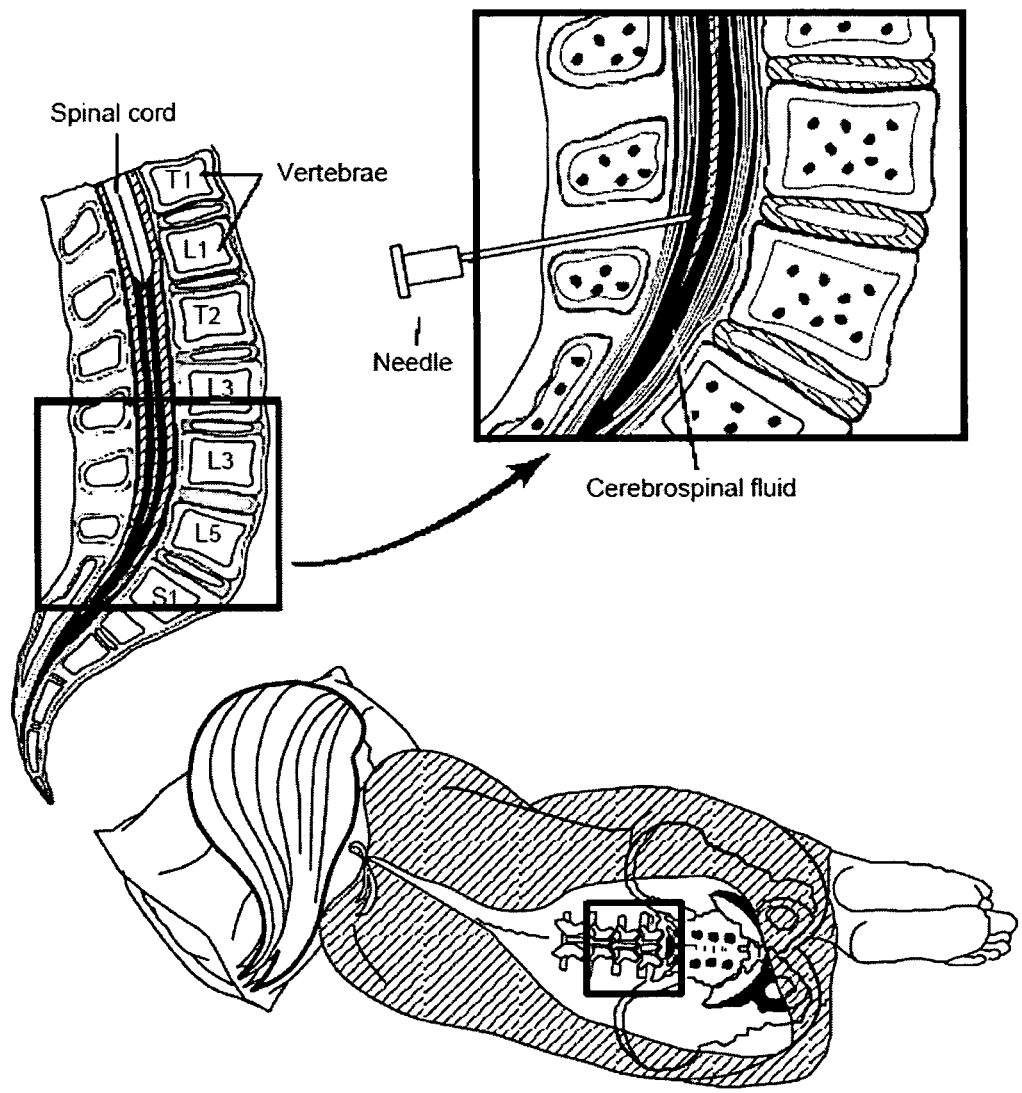
FIG. 1C depicts an exemplary approach for inserting a needle into a patient's back to perform a lumbar puncture.

General aspects of a spinal canal access procedure and basic tissue anatomy are described with reference to FIGS. 1A through 1C. The spinal canal includes both the epidural space as well as the subarachnoid space containing CSF, with those two spaces separated by the dura. In an access procedure, a needle (or other probe) is inserted through the skin and subcutaneous tissue and into a tough ligament in the patient's back. In a lumbar puncture procedure, the needle advances through the ligament and into the epidural space, and further through the dura into the subarachnoid space for access to the CSF (e.g., FIGS. 1A and 1C). Precision and care is required in needle positioning, not only to ensure that the needle reaches the CSF target area/tissue but also in preventing the needle from advancing too far distally and into the blood vessels (i.e., bloody tap). In an epidural access procedure, a needle is similarly advanced into the skin and subcutaneous tissue, and through the ligament, and into the epidural space (FIGS. 1A and 1B). Though, it is desirable in an epidural access procedure that the needle is prevented from advancing through the epidural space so as to avoid puncture through the dura and into the CSF.

Thus, in one aspect, the present invention includes structures and methods for performing a lumbar puncture procedure. A detection device of the present invention can include a pressure transducer and display (e.g., housing integrated display) that allows a user/physician to use pressure sensing to rapidly identify entry of a probe (e.g., needle) into the CSF space, as well as rapid or simultaneous identification and monitoring of pressure (e.g., opening pressure). Devices herein can further allow user identification of entry into the CSF space by detection and/or display of a pressure waveform characteristic to the subarachnoid space. The pressure waveform, like any detected pressure herein, can be detected quite rapidly and reported to the user (e.g., a few hundred milliseconds upon CSF entry), much faster than the time required for the CSF to come out the end of the needle. Thus, methods and devices herein allow physicians or other users to more quickly, precisely, and confidently identify needle entry into the CSF space.

As discussed further below, a detection device for spinal canal access procedure (lumbar puncture, epidural, etc.) typically will include an "in-line" assembly or design, where the needle/probe is coupled to the device main body or housing, with the needle and the housing disposed substantially along the same long axis or axially arranged in sequence. Such a configuration can provide numerous advantages, such as facilitating better visualization of the needle, the display (e.g., on a top side of a hand-held housing) and the patient during a procedure. Further, the needle will typically be rigidly coupled to and in relatively close proximity to the housing in the user's hand, thereby facilitating more precise control of needle positioning by a single user additionally monitoring pressure readings.

In use, a device is provided together with a spinal or epidural needle and typically a syringe (in the case of an epidural procedure), and the needle is inserted into the ligaments in the back. The needle is rigidly attached to a distal portion of the device such that manipulation of the hand-held device/housing allows user control of the positioning of the attached needle. The device further includes a hub or port for coupling the syringe (e.g., on a proximal portion of the housing). The device and attached needle assembly is advanced distally and through the ligaments and toward the spinal canal (e.g., CSF, epidural space). See also, FIGS. 1A and 1B generally illustrating tissue anatomy and needle positioning in a lumbar puncture procedure.

As the needle enters the CSF space, an increased pressure reading on the detection device will be detectible and indicative of CSF space entry. For example, a pressure reading may jump from about 0 cm $H_2O$ in the tissue or ligament to a higher pressure of the CSF (e.g., about 5-30 cm $H_2O$ with a pulsation of 3-5 cm $H_2O$). Such increased pressure reading indicating correct positioning of the needle in the CSF space typically occurs well before spinal fluid reaches the needle hub for visualization. With better confirmation of successful needle entry into the CSF space, the need for additional needle manipulation is reduced and the chance of a bloody tap is greatly reduced.

Methods and devices herein can further include monitoring of spinal canal pressure following confirmation of entry. For example, the device allows rapid detection of an opening pressure upon entry of the needle into the CSF. This rapid opening pressure measurement reduces procedure time, Since, as noted above, opening pressure measurement previously involved use of a cumbersome manometer assembly and waiting for the CSF to slowly fill up the column, rapid opening pressure measurement per the current invention significantly reduces procedure time. Health care providers can collect the CSF samples, note the closing pressure, and finish the procedure in a more efficient and timely manner, thereby reducing labor as well as risks associated with the procedure. Increased time efficiency can be especially important in pediatric patients, to whom the procedure can be quite traumatizing. Additionally, the methods and devices herein reduces the number of healthcare providers needed for the procedure, as even a single physician can perform most, if not all the necessary functions. Furthermore, the device allows additional monitoring of pressure as often as desired during and at the end of the procedure, thereby allowing a more rapid and convenient determination of when a desired closing pressure has been reached. Such time efficiency and monitoring advantages may help prevent over-drainage of CSF when a large volume is required.

Lumbar puncture methods and devices herein can further be utilized in the diagnosis and treatment of diseases or conditions related to altered or abnormal CSF pressure or volume. For example, devices herein can be used in diagnosis of Idiopathic Intracranial Hypertension (IIH), also known as pseudotumor cerebri. IIH is a syndrome of increased intracranial pressure without a known cause. The incidence of chronic IIH in overweight women, 20-40 years old, is 20 in 100,000. To diagnose IIH, a lumbar puncture must be performed, and an opening pressure of greater than an indentified threshold value (e.g., 250 mm $H_2O$) needs to be documented. Making the measurement of opening pressure easier will encourage more physicians to perform lumbar punctures to assist in the diagnosis of this disease. First line treatment of the disease is removal of CSF. However, when an elevated opening pressure is discovered, CSF should be removed slowly and the pressure monitored during the procedure. No additional CSF should be removed once the pressure reaches 50 percent of the opening pressure. Thus, devices and methods herein can be utilized in diagnosing and/or treating IIH, and for monitoring pressure during the therapeutic removal of CSF in these patients.

Devices and methods herein can further include diagnosis, treatment, or management of post dural puncture headaches following lumbar puncture. It is generally believed that the headache is caused by intracranial hypotension due to a reduction in CSF volume. Injections of saline into the CSF space can restore CSF volume, increase CSF pressure, and alleviate post dural puncture headache. Methods herein further include use of the disclosed devices to manage or treat post dural puncture headaches, and can include measurement of closing pressure, as well as facilitating replacement of lost CSF with sterile saline in patients with significantly reduced pressure, thereby treating or helping decrease the occurrence of post dural puncture headaches following routine lumbar puncture.

In another aspect, the present invention includes structures and methods for performing an epidural procedure. Such a procedure will generally include gaining access or positioning, or monitoring positioning, of a needle or catheter in the epidural space of a patient's spinal canal. For example, devices can rapidly measure pressure (e.g., essentially in real-time) during the insertion of epidural needles in guiding the entry of the needle into the epidural space. General device construction includes a generally hand-held sized housing with pressure sensing components and electronics, as well as a visual display for reporting pressure readings/detections to the user. The device includes a distally positioned port that can couple to probe, e.g., needle or a positioned catheter, for obtaining a pressure reading of a tissue environment in which the probe/needle/catheter is disposed. A device further includes a syringe coupling port, generally disposed opposite the probe port or on a proximal portion of the device. As discussed further herein, the device typically will include the "in-line" assembly or design, wherein certain components of the device such as the needle and the housing are disposed substantially along the same long axis or axially arranged in sequence.

In use, the operator (e.g., physician) can first insert the epidural needle into the tough ligament in the back. The device can then be coupled to the needle and slightly pressurized (e.g. 100 mm Hg) with a media such as air or saline using a syringe connected (should you say coupled instead of connected for consistency sake) to the device. The needle is advanced, e.g., via manipulating positioning of the device, through the ligament until it enters the epidural space. As the needle enters the epidural space, the media will exit the end of the needle and the pressure will rapidly drop, signaling entry into the epidural space through the output of the visual display.

Similar to above, the device can further signal identification of entry into the epidural space by detection and/or display of the pressure waveform characteristic to the epidural space. A false loss of resistance (and a drop in the pressure) could occur if the needle enters the surrounding tissue (e.g. muscle), however, the characteristic pressure waveform would not be present in such a case. Thus, present methods and devices allow identification of such false loss of resistance or needle entry into muscle tissue.

Methods herein further allow identification, during an epidural procedure, of accidental entry into the CSF space. For example, user error occurs where the operator accidently inserts the needle too far distally and enters the CSF space, which will also exhibit the pressure waveform characteristic of the spinal canal. The waveforms in the epidural space and the subarachnoid space are very similar and difficult to differentiate. To distinguish the epidural space from the CSF space or a vein, the operator can aspirate slightly to look for a return of CSF fluid or blood, which would indicate entry of the needle into the CSF space or a vein, respectively. The absence of any fluid, together with pressure readings indicative of spinal canal positioning, would indicate that the needle is likely in the epidural space. See also, FIGS. 1A and 1C generally illustrating tissue anatomy and needle positioning in epidural procedure.

In one embodiment, devices herein may be used to confirm or monitor positioning of an epidural catheter. Currently, correct placement of the epidural catheter is generally confirmed using a test dose of local anesthetic, but this method has a number of limitations. According to an embodiment of the present invention, the detection device can be coupled with an epidural catheter for monitoring or detection of pressure in the environment in the patient's tissue and about the catheter. If the catheter is placed correctly, a pressure waveform should be evident or detectable. The absence of a waveform suggests that the catheter is misplaced. A small injection of saline (e.g. 5 cc), for example, can help make the waveform more evident. Using the detection device to confirm correct catheter placement can help avoid complications as well as reducing procedure time, leading to more rapid administration of anesthesia and more efficient use of medical resources (e.g., facilities or equipment use, physician time, etc.). Further, such a method can increase quality of care by reducing or eliminating a period of time when a patient may not have pain relief because of a misplaced catheter. Additionally, the catheter position can be confirmed while the patient is still under general anesthesia, which is not possible with anesthetic test dosing technique.

As may be apparent, in performing a lumbar puncture, the needle passes through the epidural space before entering the CSF space. In epidural needle placement, the needle is placed in the epidural space, but advancement too far is undesirable and will result in dural puncture and entry into the CSF space. Additionally, a needle used for an epidural procedure is typically much larger than a lumbar puncture needle, and the former is therefore more likely to cause a significant (i.e., larger) CSF leak if it punctures the dura and more likely to cause the post dural puncture headaches. FIG. 1A illustrates how the needle could enter the muscles if it exits the midline, where the ligament sits. The entry of the epidural needle into this muscle can often be interpreted as a "loss of resistance" and, absent pressure readings, the physician may mistakenly insert the catheter into the muscle, resulting in failed anesthesia.

Different types of probes or objects, for example, needles, catheters, tubes, and the like can be inserted into a human or animal body for various medical purposes or indications. Accurate placement or positioning of such objects within the body is generally required. For instance, during lumbar puncture or epidural anesthesia procedures, it is important to place a needle or catheter into the space necessary to perform the given procedure, e.g., the subarachnoid space or the epidural space.

Embodiments of the present disclosure are directed to systems, devices, apparatuses, methods, and processes for facilitating, indicating, and/or verifying access to at least one type of target or intended anatomical environment, substance, site, location, structure, tissue, organ, cavity, and/or lumen. Particular embodiments are further directed to systems, devices, apparatus, methods, and processes for indicating or verifying access to at least one type of non-target, unintended, or inadvisable anatomical environment (e.g., in view of a medical procedure directed to the target anatomical environment). Embodiments of the present disclosure can include or involve systems, devices, apparatuses, methods, or processes for detecting, sensing, capturing, measuring, and/or analyzing one or more substances or signals associated with particular physiologic parameters or conditions to facilitate the identification, evaluation, or verification of a location of a portion of an object within a body (e.g., relative to a target or intended anatomical site).

Several embodiments of the disclosure are directed to categorizing or distinguishing between aspects of one or more anatomical substances or sites, for instance, to differentiate or indicate a difference between a first or target anatomical site and a site other than a target anatomical site (e.g., a second or non-target anatomical site); or to determine or indicate whether an anatomical substance originates from or was supplied by, extracted from, or acquired at a first or target anatomical location or structure or a second or non-target anatomical location or structure. Such embodiments can facilitate an automatic or semi-automatic verification or notification that a portion of an object inserted into a body has transitioned into, resides at or within, or has transitioned away from a target substance or site, or one or more non-target substances or sites. Particular embodiments of the disclosure are directed to distinguishing between spinal canal and non-spinal canal, as well as between aspects of one or more of a ligament, paraspinal muscle, an epidural space, blood vessel, and/or a subarachnoid space.

The presence, absence, relative or absolute level, or change in a physiological parameter (e.g., pressure) can directly or indirectly correspond to an anatomical location or environment at which a portion of the probe resides, and/or a patient state or condition. The system or apparatus may optionally additionally include a processing unit configured to a) generate physiologic parameter values using signals output by the set of sensors; and b) analyze or evaluate particular physiologic parameter values. The system or apparatus further includes an output unit configured to generate at least one type of feedback (e.g., audio and/or visual feedback) that indicates whether a portion of the probe under consideration is exposed to or resides at a first or target anatomical site or substance, or a second or non-target anatomical site or substance. In various embodiments, each of the processing unit and the output unit can be carried by the housing, which can be a single use or disposable structure (e.g., a disposable cartridge).

Representative aspects of embodiments of systems, apparatuses, devices, and processes of the present invention are described in detail hereafter with reference to the identified figures. The description herein provides for embodiments that are suitable for indicating successful or unsuccessful lumbar puncture, epidural space, or cerebrospinal fluid access; and embodiments suitable for other medical indications.

Figure 2:
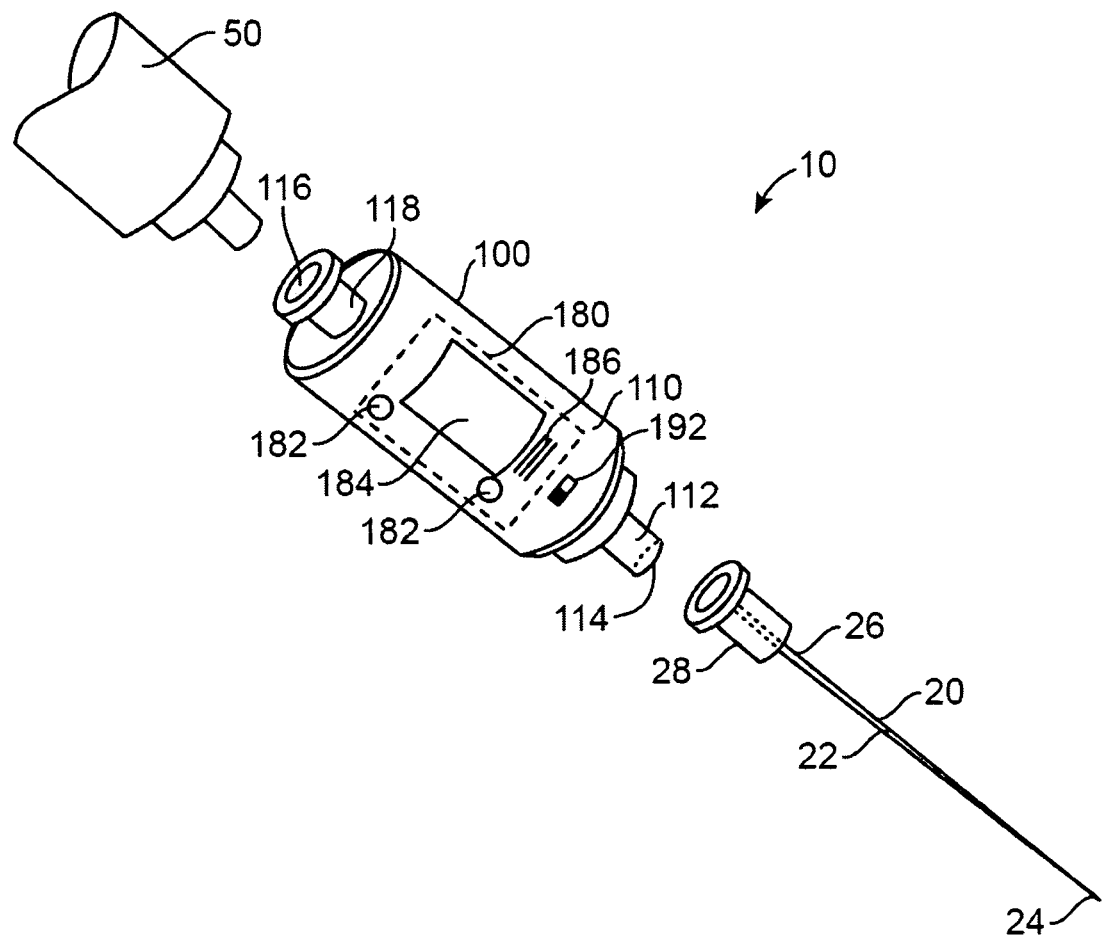
FIG. 2 is a perspective illustration of an apparatus for indicating a probe segment or probe tip location according to an embodiment of the disclosure.

FIG. 2 is a perspective illustration of an apparatus 10 for indicating a probe tip location or environment according to an embodiment of the disclosure. In an embodiment, the apparatus 10 includes a probe site indication device (PSID), probe tip location device (PTLD), or anatomical environment characterization device (AECD) 100 (hereafter "device" or "detection device") that is coupled to a probe such as a needle 20. The needle 20 includes an elongate member or shaft 22 having a first or insertion end or distal tip 24 and a second or proximal end 26. The needle's shaft is hollow, that is, the needle's elongate member includes a bore that extends between the needle's tip 24 and its proximal end 26. The needle's proximal end 26 can be coupled to a conventional needle coupling or fitting structure 28, such as a Luer adapter, connector, sleeve, collar, or lock. In certain embodiments, the apparatus 10 can further include a syringe 50 that can be coupled to the detection device 100, for instance, by way of a conventional syringe coupling or fitting such as a Luer adapter, connector, sleeve, collar, or lock.

Figure 3A:
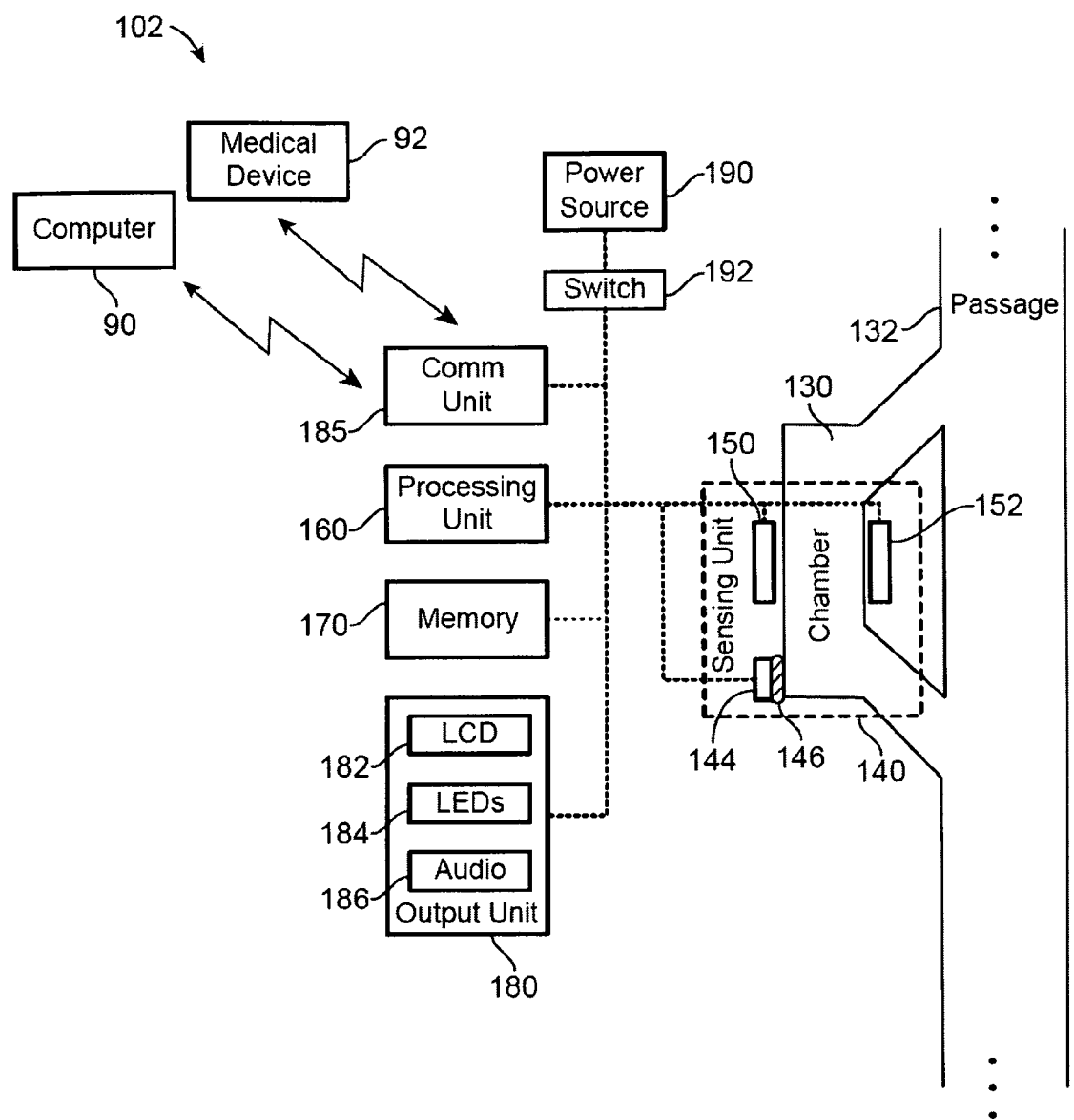
FIG. 3A is a block diagram of a system according to another embodiment of the disclosure.

FIG. 3A is a block diagram of an detection device 100 according to an embodiment of the disclosure. With simultaneous reference to FIG. 2A, in various embodiments the detection device 100 includes a housing 110 that carries a first coupling structure 112, a first opening or port 114, at least one fluid or substance detection or analysis chamber or corridor 130 (e.g., a flow-through chamber 130), a sensing unit 140, a processing unit 160, a memory 170, an output unit 180, a power source 190, and an activation switch 192. In some embodiments, the housing 110 can additionally carry a passage 132, a second opening or port 116, and a second coupling structure 118. Each of the sensing unit 140, the processing unit 160, the memory 170, and the output unit 180 are coupled to the power source 190 by way of the switch 192. Selection of a predetermined switch position or a switch toggle can activate the detection device 100. In an embodiment, the power source 190 includes a battery or a capacitor configured to power the detection device 100 for a predetermined or expected total amount of time (e.g., at least a few minutes to a few hours, approximately 2 hours, approximately 12 hours, approximately 1 day, or another amount of time).

The first coupling structure 112 carries the first port 114, and includes one or more coupling, fitting, securing, retaining, or connecting elements configured to mate with a given type of probe or needle 20. Similarly, the second coupling structure 118 carries the second port 116, and includes one or more coupling, fitting, securing, retaining, or connecting elements configured to mate with another medical implement such as the syringe 50. One or both of the first and second coupling structures 112, 118 can include or be, for instance, a Luer adapter, taper, collar, slip, connector, or lock structure. For instance, the first coupling structure 112 can include a male Luer lock fitting, and the second coupling structure 118 can include a female Luer lock fitting. In an embodiment, the first and second coupling structures 112, 118 are carried at opposite sides or ends of the housing 110. Each of the first and second coupling structures 112, 118 can carry a removable or pierceable/penetrable end cap or seal (not shown) to facilitate the maintenance of a controlled environment within the device 100.

In an embodiment, the chamber 130 includes or forms a cavity or compartment into which a fluid or substance can flow or be drawn, and the passage 132 includes or forms a channel or bore through which the fluid or substance can flow or be drawn. The chamber 130 and the passage 132 are fluid communicable or in fluid communication with the bore of the needle 20 by way of the first port 114. The passage 132 extends between the first port 114 and the second port 116, and hence the second port 116 is fluid communicable or in fluid communication with the bore of the needle 20 by way of the passage 132. Upon insertion or injection of the needle 20 into an individual's body, a bodily fluid such as blood can flow or be drawn from the tip 24 of the needle into the chamber 130 and the passage 132. The bodily fluid can further flow or be drawn through the passage 132 into the syringe 50.

The sensing unit 140 includes a set of sensors, sensing devices, or sensing elements in sensing communication with the chamber 130. More particularly, the sensing unit 140 is in signal and/or substance communication with the chamber 130, such that the set of sensing elements can directly or indirectly apply signals to a substance within the chamber, detect or measure particular properties of a substance present within the chamber, and/or subject a substance within the chamber to one or more tests. Particular sensing elements may detect, measure, or test a property of a substance within the chamber in a manner that avoids direct contact with the substance, while other sensing elements may detect, measure, or test a property of a substance within the chamber by way of direct access to or physical contact with the substance. The chamber 130 can include one or more openings, windows, or ports to facilitate direct access to or physical contact with a substance carried within the chamber 130.

Particular sensors or sensing devices generate sensing signals that correspond to one or more physiologic properties of a substance within the chamber 130 at a particular time. Depending upon the nature or characteristics of a given set of sensing signals, the set of sensing signals may directly provide a value or measure of a physiologic parameter, or the set of sensing signals may be a correlate or partial correlate of the physiologic parameter. If a set of sensing signals provides one or more physiologic parameter correlates or partial correlates, a number of mathematical operations can be applied to at least a subset of signals within the set of sensing signals to generate, determine, or estimate at least one physiologic parameter value.

Any given sensing device operates in accordance with a sensing device modality, which corresponds to a type of signal that the sensing device is configured to acquire and/or a type of physiologic measurement that can be generated or obtained using the sensing signal. A particular sensing device can operate in accordance with a modality such as pressure sensing, optical sensing, temperature sensing, fluid dynamics sensing, chemical or biological species sensing, or another modality. Depending upon embodiment details, the set of sensors or sensing devices can include one or more light emitting diodes (LEDs), semiconductor lasers, optical detectors (e.g., photodiodes, which can be configured to detect optical signal characteristics such as intensity, peak wavelength, or phase shift), pressure sensors (e.g., a diaphragm and/or a pressure transducer such as a piezoelectric transducer), temperature sensors (e.g., an optical temperature sensor or a thermocouple), fluid flow sensors (e.g., a Doppler ultrasound transducer and detector), substance or environment sensing field effect transistors (e.g., a chemical sensing or chemically modified FET (ChemFET), an ion sensitive FET (ISFET), an Enzyme modified FET (EnFET), or an electrolyte-oxide-semiconductor FET (EOSFET)), an electrophoresis device, a biological microchip (e.g., a biochip) or a microfluidic lab-on-a-chip (e.g., as described by Rohit Pal et al. in "An integrated microfluidic device for influenza and other genetic analyses," *Lab on a Chip*, Royal Society of Chemistry 2005, 5, 1-9), and/or other sensing elements or devices.

In an embodiment, with respect to sensing pressure related parameters (e.g., for a lumbar puncture or epidural procedure), the set of sensing elements can include a pressure sensor or pressure sensing system, e.g., such as a piezoelectric pressure transducer 144 coupled to a diaphragm 146 that is exposed to an opening in the chamber 130. When the chamber 130 is in communication (direct or indirect) with tissue or fluid source, anatomical pressure exerts a displacement force upon the diaphragm 146. The diaphragm 146 in turn exerts a force upon the piezoelectric pressure transducer 144, which generates an electrical signal corresponding to an instantaneous, quasi-instantaneous, or near-instantaneous pressure reading at a distal probe segment or the probe tip 24.

The sensing unit 140 is configured to output signals (e.g., sensing signals) to the processing unit 160 and/or the memory 170 on a continuous or periodic basis, and/or in response to one or more sensed parameter values exhibiting a change that exceeds a predetermined magnitude relative to one or more previously sensed parameter values. With respect to the above described embodiment directed to indicating pressure for spinal canal access and/or monitoring, the sensing unit 140 can store and/or output a series of instantaneous or near-instantaneous pressure values and/or a set of measured values in the memory 170.

The processing unit 160 can include a state machine, a microcontroller, a microprocessor, an application specific integrated circuit (ASIC), or a field programmable gate array (FPGA) or programmable logic device (PLD) configured to correspond to or execute program instruction sequences (e.g., software and/or firmware) directed to receiving, operating upon, evaluating, analyzing, interpreting, and/or transforming signals generated by one or more portions of the sensing unit 140, and determining whether the tip 24 of the needle 20 resides within a target anatomical site, structure, or substance. In an embodiment, particular program instruction sequences can additionally or alternatively be directed to determining whether the needle tip 24 resides within one or more non-target, undesirable, or inadvisable anatomical sites, structures, or substances. Furthermore, such program instruction sequences can be directed to determining whether the needle tip 24 has transitioned into, resides within, or has transitioned away from one or more intermediary tissues or anatomical environments along a needle insertion trajectory toward a target anatomical destination or environment. In certain embodiments, particular structural portions or operational aspects of the processing unit 160 can be included or incorporated within the sensing unit 140.

In an embodiment, a given type of sensing device operates in accordance with a particular sensing modality and generates a particular type of sensing signal, which depending upon sensing device or sensing signal type can directly or by way of mathematical correlation or transformation provide a physiologic parameter value and hence an indication of a probe tip position. The processing unit 160 can use or mathematically operate upon a set of sensing signals corresponding to a given type of sensing device to determine a single type of physiologic parameter value, or multiple distinct types of physiologic values that differ from each other by way of a set of mathematical operations. For instance, the processing unit 160 can generate a mean value of a physiologic parameter using a time series of sensing signals generated by a given type of sensing device. Additionally or alternatively, the processing unit 160 can additionally or alternatively generate a maximum or mean value of a physiologic parameter fluctuation, range, amplitude, or magnitude using this time series of sensing signals. The processing unit 160 may process received pressure value signal for recognition of a pattern recognition, such as recognition of a pressure waveform characteristic of the spinal canal. As a representative example, the processing unit 160 can average a series of sensed instantaneous vascular pressure values to determine a mean pressure value with respect to a predetermined time period (e.g., fraction of a second, approximately 1-10 seconds, 30 seconds, 1 minute, or longer). The processing unit 160 can additionally or alternatively determine a maximum and/or average pressure fluctuation value relative to a predetermined time period.

Devices of the present invention can be configured for operation in one or more of various different operational modes. In one embodiment, a device is operable in a tissue transition detection mode ("transition detection mode"). For example, the device can be configured to detect probe or needle distal tip location during blind needle insertion. In such operation, the pressure changes rapidly when the needle (e.g., probe) transitions from one site to another, provided the two sites have different pressures (e.g. from soft tissue to a vessel, from a vein to an artery, from a ligament to the epidural space, from a ligament to the CSF space). It has been observed that the pressure change at the tip of the needle is transduced through the air (or vacuum) already present in the device housing, and therefore an absolute pressure reading is available before the arrival of the body fluid. The device display can be used to indicate tissue transitions, with the device configured such that the display updates at an appropriate rate. If the display updates at a constant rate (e.g. at 4 Hz), or if the display is displaying average pressure, rapid pressure changes may not be easily discerned by the user in some indications. Rather, a variable display rate makes pressure changes more apparent by introducing sudden, non-cyclical display changes that "stand-out" visually. For instance, if the probe is in soft tissue (e.g., pressure~0 mm Hg), the display can update at 1 Hz. A near instantaneous (e.g. within 5 ms) change in the display reading upon entry into a vessel (e.g. from 0 mm Hg to 25 mm Hg) can provide a visual cue to the user that a tissue boundary has been crossed. The device makes use of algorithms developed to determine when to update the display given a temporal set of pressure readings. In general, when the needle tip is in a static environment (e.g. in an artery), the display provides a mean pressure, using a moving average of the pressure readings over a given time period. However, if the needle is removed from a vessel, the display immediately reverts to an instant reading.

In another embodiment, a device can be configured for continuous monitoring at fixed location ("continuous monitoring" or "fixed location" mode). During continuous monitoring, different values of pressure are useful to the user, especially the mean pressure over a period of time, or the maximum and minimum values over a given period of time (i.e. systolic and diastolic pressure). Further embodiments may include a combination of different operation modes. For example, in some indications (e.g., vessel access, lumbar puncture, epidural catheter insertion), it may be desirable to switch (e.g., programmed or automatic switching) between these two modes—blind needle insertion and continuous monitoring.

The memory 170 can include an electronically or computer programmable or readable medium having one or more of a Random Access Memory (RAM), a Read Only Memory (ROM) such as a type of programmable ROM (PROM), a set of registers, or other data storage elements for storing a) program instruction sequences; b) signals generated or output by the sensing unit 140 or physiologic parameter values corresponding thereto; and c) reference data that facilitates the determination, evaluation, or analysis of sensed physiologic parameter values. For instance, the memory 170 can store pressure waveform pattern data or a set of program instructions can access to facilitate the evaluation or analysis of sensed pressure values for identification or detection of spinal canal pressure waveform. The memory 170 can also store data (e.g., in a data structure such as a lookup table) that a program instruction sequence can access to a facilitate an assignment or mapping of a set of sensed physiologic parameter values to a categorization of the needle tip's location with respect a target, a non-target, and/or an intermediary anatomical structure or substance, as further detailed below. In association with the execution of one or more program instruction sequences, the processing unit 160 issues or transfers reporting signals to the output unit 180 to facilitate the provision of visual and/or auditory feedback corresponding to the needle's sensed location. In various embodiments, the reporting signals can indicate whether a needle portion such as the tip 24 resides at a first/target anatomical location (e.g., by way of a first set of reporting signals), or a second/non-target anatomical location (e.g., by way of a second set of reporting signals that are perceptually different than the first set of reporting signals), as further detailed below. In one embodiment, the reporting signals can further indicate whether the needle resides at neither a first/target anatomical location nor a second/non-target anatomical location (in which case the needle may reside at an anatomical location that is unrelated to the first/target anatomical location and the second/non-target anatomical location). Particular aspects of processes that can correspond to an automated sequence (e.g., performed by way of program instruction execution) directed to presenting physiologic parameter values to a user (e.g., a surgeon or other medical professional) or observer and/or indicating a position of a probe segment or tip 24 relative to a target, non-target, and/or intermediary anatomical site or structure are described further herein.

In response to the reporting signals, the output unit 180 is configured to generate and actively provide or convey visual and/or auditory signals that can indicate (e.g., in a selective manner) whether the needle resides at or within a target or non-target anatomical site, structure or substance. In an embodiment, the output unit 180 actively provides or conveys a visual and/or auditory indication of a needle location by applying a non-zero amount of power to an output device, thereby activating the output device to selectively emit, radiate, or externally propagate one or more signals/set of signals that provides a user or observer with sensory feedback (visual and/or auditory feedback) indicative of pressure of the environment in which the needle is disposed and/or needle location.

Depending upon embodiment details, the reporting signals can correspond to notification signals and/or alert signals. Notification signals can indicate or provide one or more detected, measured, or estimated physiological parameter values corresponding to sensing unit operation. Notification signals can include, for instance, visual and/or auditory signals corresponding to one or more physiologic parameter values such a pressure value, and/or a pulsatility measure or a peak-to-minimum pressure difference value. Alert signals can include visual and/or auditory signals that provide a binary or "yes/no" indication or a likelihood indication (e.g., a probability based indication, as determined in association with the execution of a program instruction sequence) of an intended or appropriate probe or needle positioning. In an embodiment, alert signals can further provide a binary or "yes/no" indication or a likelihood indication of an unintended, undesirable, or incorrect probe positioning.

The output unit 180 can output multiple reporting signals in a simultaneous or non-simultaneous (e.g., sequential) manner. Notification or alert signals can be presented on an essentially continuous, sampled, or periodic basis following detection device activation, or in response to a trigger event such as a first detection of one or more physiologic parameter values that correspond to a target or a non-target anatomical needle tip placement, or a predetermined change in a physiologic parameter value.

In general, the output unit 180 can include one or more types of output devices, for instance, a user interface or display (such as a liquid crystal display or LCD) 182, a set of LEDs 184, and possibly an audio device such as a speaker 186. In an embodiment, notification signals displayed by the display 182 (e.g., on a real-time, near real-time, a periodic basis, or in response to a given amount of physiologic parameter change) can include or correspond to particular physiologic parameter value(s). The presentation of particular physiologic parameter values to a user or observer can facilitate the determination or confirmation of a probe location. Signals output to the user via the output unit or components thereof (e.g., display) are not limited to any particular type and can include, e.g., pressure values (including any number of different measurement units for pressure), messages, text, graphs, pattern recognition alert, symbols, flashing lights, audio alters, and the like, as well as any combination of any number thereof.

According to another embodiment of the disclosure, the device 102 can be configured to communicate with a remote or external device such as a computer system 90 (e.g., a desktop computer, a laptop computer, or a personal digital assistant) and/or a given piece of medical equipment 92. A communication unit 185 can optionally be coupled with the device, so as to configure a device, system, or assembly for wireless or wire-based signal transfer involving the device 102 and a remote computer system 90 and/or medical device 92, such as an ultrasound system or device (e.g., portable ultrasound unit), and the like.

Figure 3B:
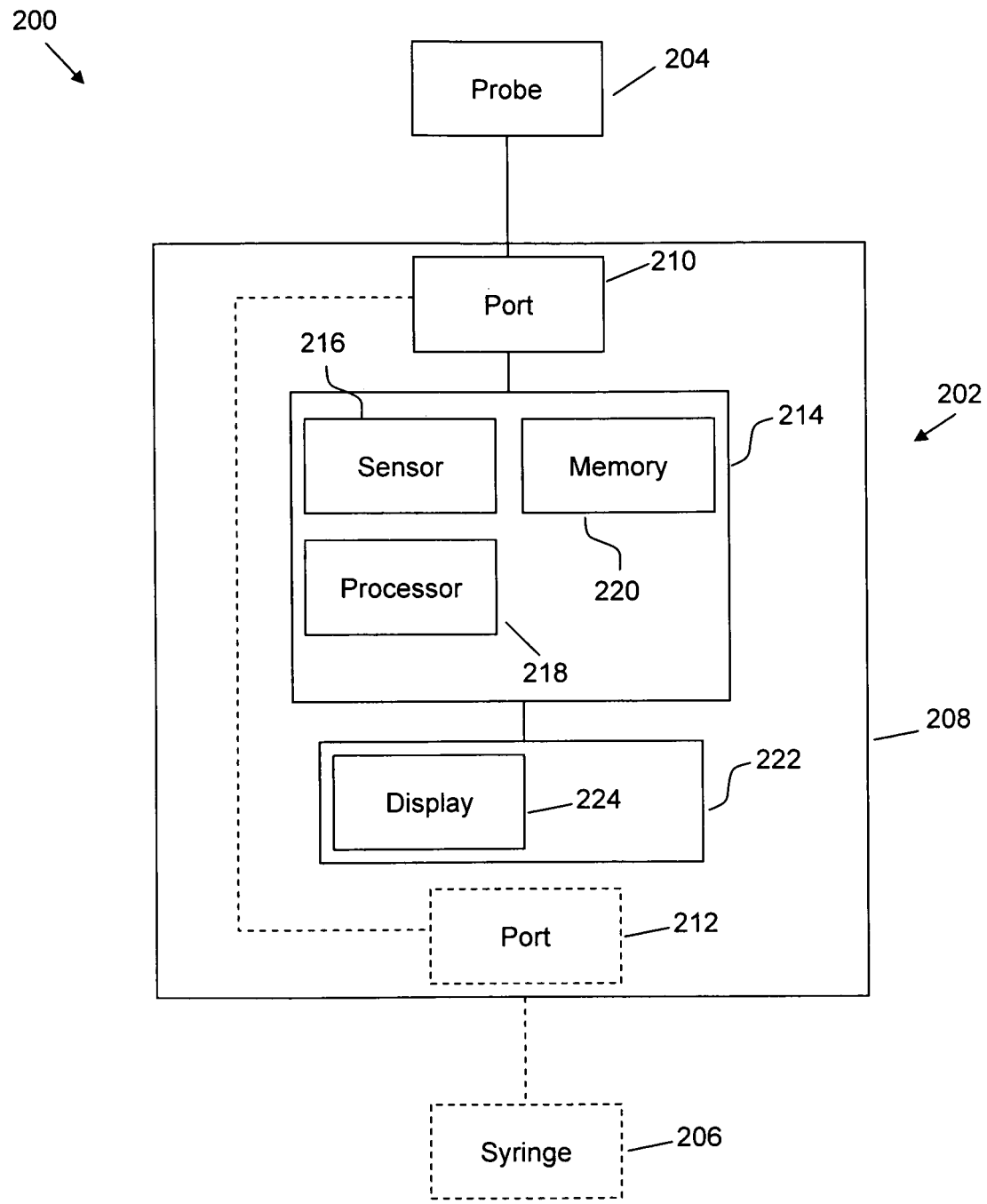
FIG. 3B illustrates a block diagram of a system according to another embodiment of the present invention.

FIG. 3B is a block diagram illustrating a detection device system or assembly, including certain components thereof, according to an embodiment of the present invention. The assembly 200 includes a device 202 couplable to a probe 204 and a syringe 206. The device 202 includes a housing 208 having a port 210 and port 212, which can generally be disposed on opposing sides or portions of the device so as to provide the general "in-line" assembly when the device is coupled together with a needle or probe 204 and a syringe 206. In a pressure sensing embodiment, the device 202 further includes a pressure sensing system 214 that will be at least partially carried by the housing 208. The pressure sensing system 214 includes at least a pressure sensor 216 and corresponding electronics, as well as internal structure or configuration, necessary for detection of a pressure value in an environment (e.g., patient tissue, fluid, vessel, etc.) in which the probe 204 is at least partially disposed. The pressure sensing system 214 may also include electronics and/or components necessary for processing, output, and/or storage of detected pressure values/signals. For example, the pressure sensing system 214 may include a processor 218 and/or memory 220. The pressure sensing system 214 further includes an output unit 222 that can include a graphical interface or display 224. The output unit 222 is at least partially carried by the housing 208 and coupled to the pressure sensing system 214 such that detected pressure values and corresponding signals can be output to the display for communication of pressure information to the user or device operator. The interface or display 224 can include a housing-integrated display that will be readily or easily visible to a device operator during use of the device. For example, the display 224 may be carried on an upper or top side of the housing, or side opposite a portion of the housing designed for hand-held gripping by the user. The display 224 may also be disposed such that a surface of the display (e.g., viewing surface) is at an angle relative to a long axis of the device/assembly (see also, FIG. 4 below). For example, the display may be angled proximally for more optimized visualization by the user. The embodiment illustrated in FIG. 3B may, though not necessarily, further include any one or more of components, aspects, or features described further herein with regard to structures or methods of the present invention.

Figure 4:
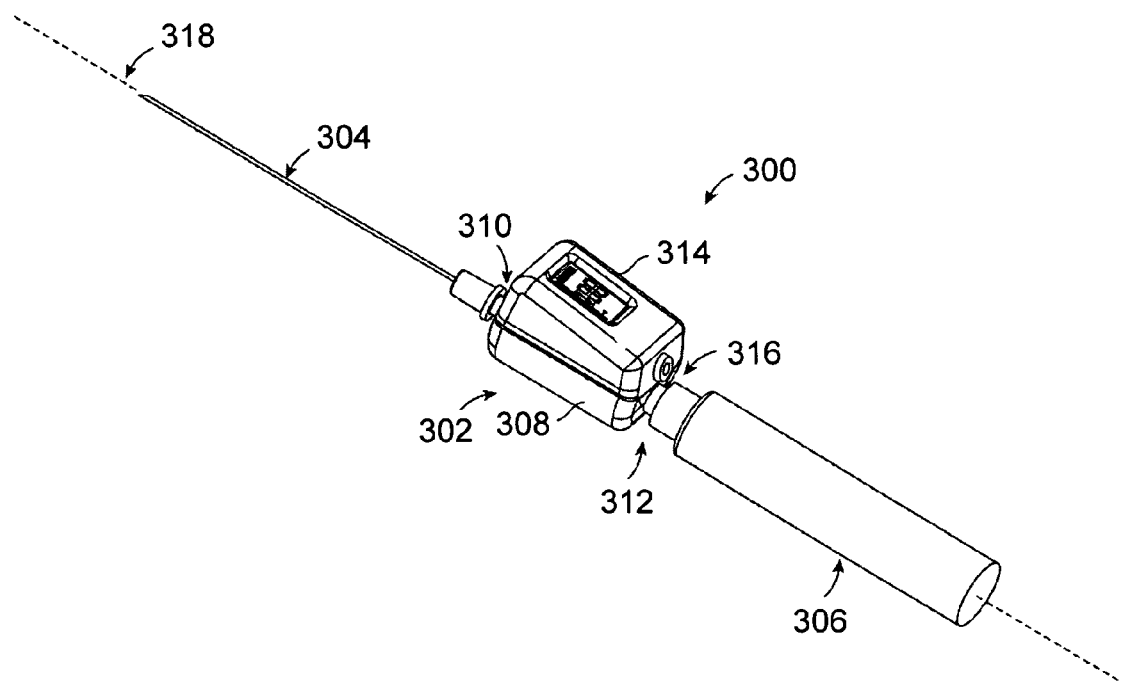
FIG. 4 illustrates an assembly including a detection device coupled to a probe and a syringe, according to another embodiment of the present invention.

FIG. 4 illustrates a detection device assembly, according to an embodiment of the present invention. The assembly 300 includes a detection device 302 coupled distally to a probe 304 and proximally to a syringe 306. The device 302 includes a housing 308 having a distal portion with a port 310 that is detachably coupled to a probe 304, and a proximal portion with port 312 that is detachably coupled to a syringe 306. Additional components, including those described above such as a sensing unit, processing unit, output unit, etc. (not shown) can be further carried by the housing 308. A housing of a device can include a single piece or multi-piece assembly. The device 302 additionally includes a display 314 for reporting or visually displaying a of a determined biological parameter, such as a pressure value.

The embodiment of FIG. 4 further illustrates the "in-line" assembly described further herein. For example, a long axis 318 of the assembly is shown to illustrate an axial alignment or in-line assembly of components, including the probe 304 and syringe 306 coupled with the device 308. Components need not be limited to any particular positioning with respect to the long axis. But axial alignment or in-line assembly will generally refer to an ordered arrangement of certain components with respect to a long axis reference. In the embodiment illustrated in FIG. 2B (and additionally in certain embodiments described further herein), the assembly includes an in-line arrangement with the device 308 disposed substantially between the coupled probe 304 and the syringe 306. Referring to the device 302, certain components (e.g., sensing unit, processing unit, output unit, display, etc.) can be carried by the housing 308 so as to be disposed substantially between port 310 and port 312. The display 314 can be carried by the housing 308 such that the display 314 or surface thereof (e.g., outer surface) is at an angle with respect to the long axis 318 of the assembly 300. For example, the display can be angled proximately as illustrated in FIG. 2B. Such a configuration of the display may be selected so as to allow a user, viewing the display from a location generally proximal to the device, to more easily view the display during operation.

In use, a user can manipulate or control positioning of the assembly while grasping or holding the assembly about the device 302 and/or syringe 306. As the probe is rigidly coupled to the device, manipulation of the device position allows control of probe positioning. The distal portion of the probe 304 can be inserted into a tissue or body of a patient. With positioning, a biological parameter (e.g., pressure) of the environment in which the probe 304 is positioned is detected or determined, and the parameter value or information output for visualization on display 314. Device and assembly operation is further described elsewhere herein.

Figure 5:
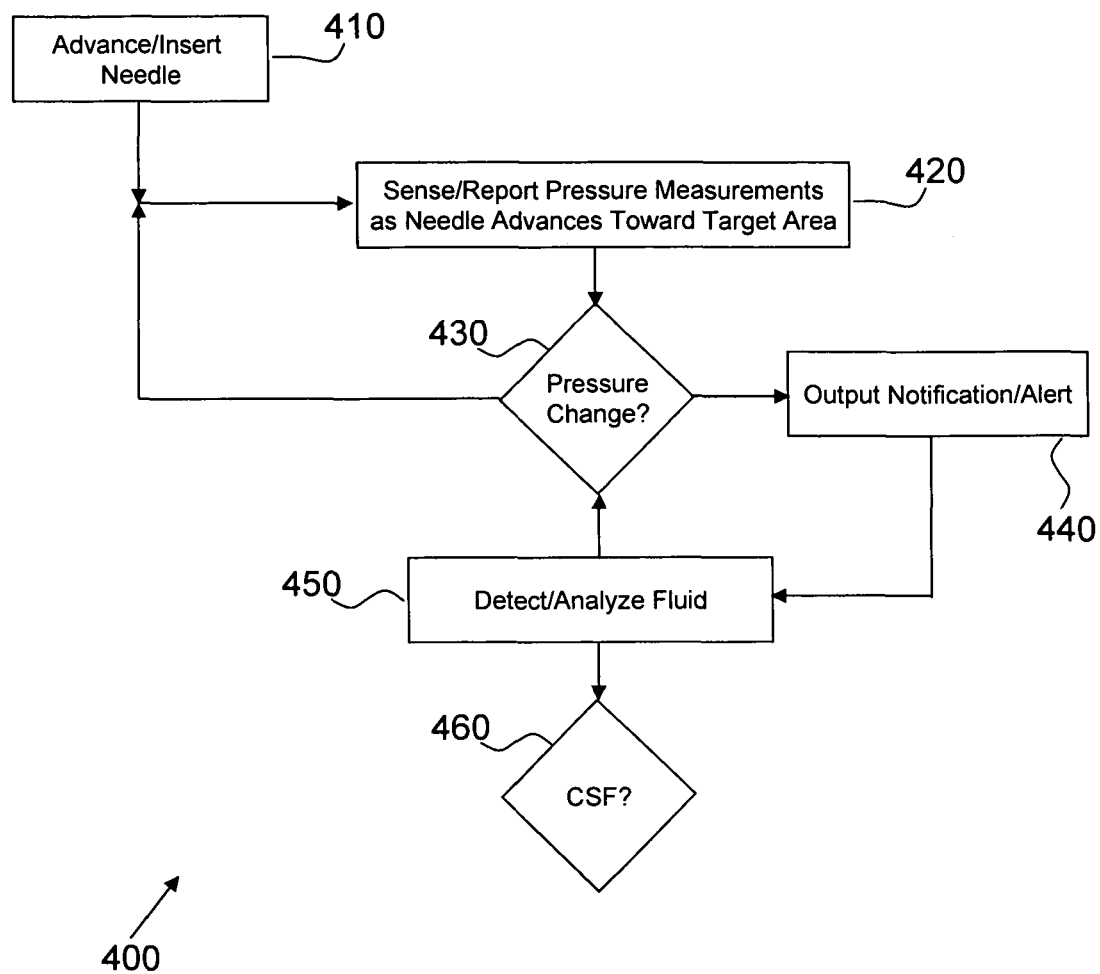
FIG. 5 is a flow diagram illustrating a lumbar puncture process according to an embodiment of the disclosure.

As previously indicated, the present invention further includes methods and structures for performing lumbar puncture procedures. A process 400 of performing a lumbar puncture procedure using a device, according to an embodiment of the present invention, is described with reference to FIG. 5. A device is provided together with a spinal needle. The needle is inserted into the desired entry point, such as into the skin and toward the ligaments in the patient's back (Step 410). The device and needle are attached, with the needle rigidly attached to the device so as to allow manipulation of needle positioning via user controlled movement of the device. The needle is then advanced distally by the user in the desired direction, such as toward the spinal canal of the patient. Pressure readings are obtained as the needle is positioned in the tissue or advanced toward the target area (Step 420). As the needle enters the CSF space, a change in pressure reading (e.g., increased pressure) will occur suggesting entry into the CSF space (Step 430). The detected pressure is output (e.g., via housing integrated interface/display) to the user for notification or alert (Step 440). The user may further detector or analyze fluid collected through positioned needle so as to confirm entry into the CSF space (Steps 450, 460). For example, fluid may be allowed to flow into the device and/or be drawn into the syringe for visualization of fluid, such as visualization of CSF fluid for confirmation of correct needle placement. A device of the present invention can additionally be utilized to measure or monitor pressure about the needle following needle placement to monitor needle positioning.

Thus, a device according to an embodiment of the present invention can be configured to serve at least one of two functions (or both): identifying entry into the CSF space, and providing a continuous pressure measurement once inside the CSF. The processing instructions and/or algorithm for the lumbar puncture application can be configured such that during the early part of the procedure, the display is in transition detection mode or a mode where the display is optimized for detecting transition of the needle tip from the ligament into the CSF space. Pressure change indicating tissue transition can be an increase or decrease, depending upon configuration and/or use of the device. For example, if no pressure is applied, the pressure will transition from a low (0 mm Hg) pressure reading to a higher or positive pressure reading (e.g. 10 mm Hg) between the ligament and the CSF space. If positive pressure is applied when the needle is in the ligament (the fluid and/or air are prevented from leaving the needle tip when it is in the ligament) the pressure will go from a high (e.g. 50 mm Hg) value to a lower positive value (e.g. 10 mm Hg) upon entry in the CSF space. Once the needle has entered the CSF space, the display can provide a mean or peak CSF pressure (the "opening pressure") and a "closing pressure" after CSF samples are removed. The graphical part of the display will demonstrate the pulsations of the CSF—i.e., the characteristic pressure waveform. The device may be programmed or configured to recognize (e.g., via processing) the waveform pattern and alert the user upon detection. The device can monitor the instant pressure, and can alert the user to needle dislodgment via the rate of the display update and the type of pressure data displayed on the device. During procedures where CSF is removed to decrease the intracranial pressure, the device provides the ability to monitor the CSF pressure, e.g. in real-time or near real-time.

A device may be further sized or optimized for pediatric lumbar puncture. In such an embodiment, the device is modified (e.g., reduced) in size and weight (e.g. by using flexible circuits and display, etc.) so that it does not dislodge the spinal needle if it is not supported by the user.

The present invention further provides structures and related methods for detection of an epidural space, e.g., during epidural access procedures such as catheter placement and drug delivery. In one embodiment, the device can be used to better prevent two common mistakes—entry of the needle into the CSF, which causes severe headaches, and mistaking the muscle or other soft tissue for the epidural space, which results in failed anesthesia (the epidural catheter is mistakenly inserted into the muscle instead of the epidural space).

Figure 6:
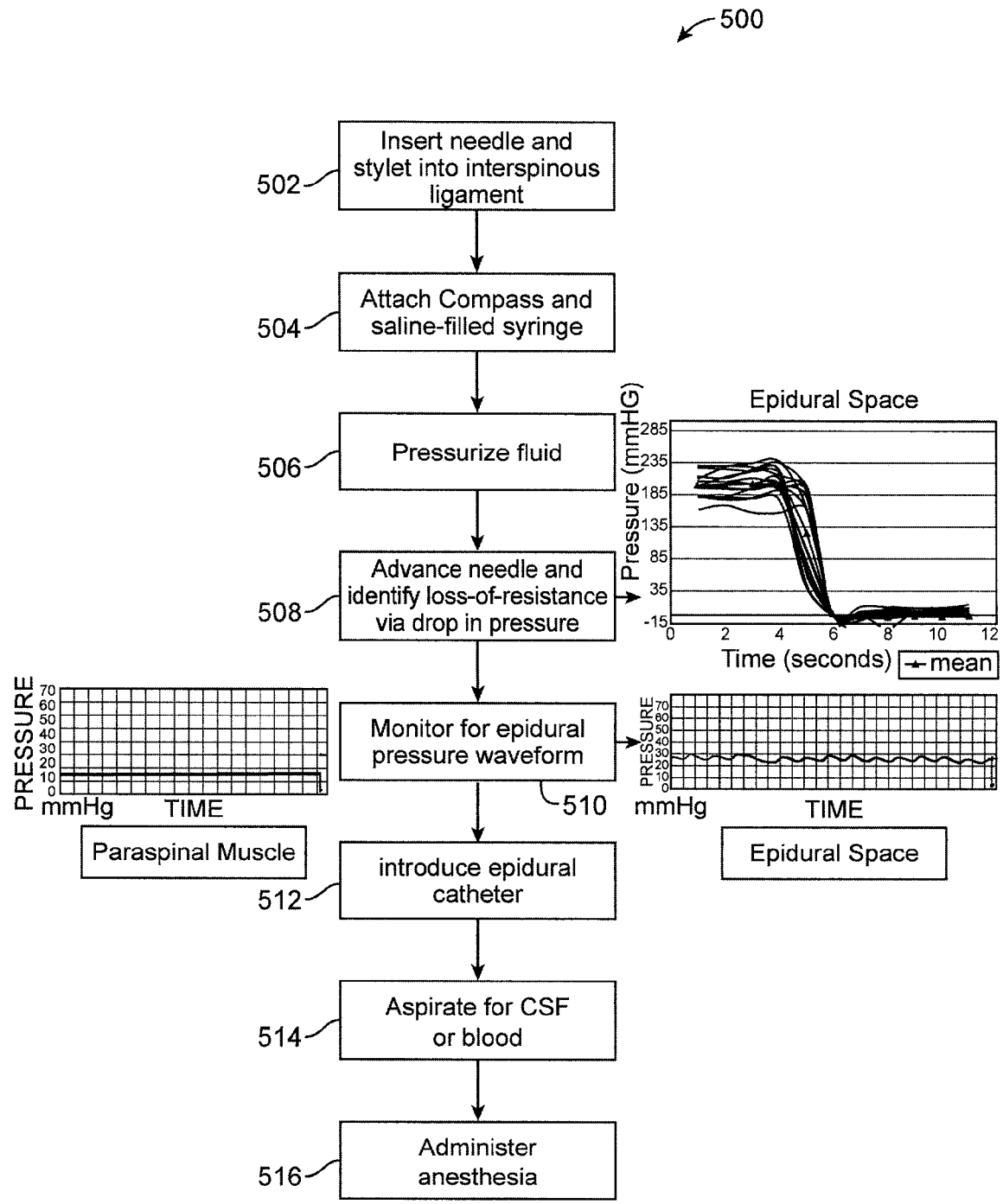
FIG. 6 is a flow diagram illustrating an epidural access procedure, according to an embodiment of the present invention.

A process 500 of performing a epidural access procedure using a device, according to an embodiment of the present invention, is described with reference to FIG. 6. A device of the present invention is provided, as well as a needle for coupling to the device. The needle (e.g., needle with stylet) is inserted into the tissue of the patient at the desired location (Step 502). The device is coupled to the needle (Step 504) and pressurized, e.g., with a media such as air or saline using a syringe connected to the device (Step 506). During an epidural procedure, the needle passes through the skin and fat, ligament, and finally enters the epidural space. Upon entry into the epidural space a "loss-of-resistance" or change in pressure will occur (Step 508). With epidural space entry, the media will exit the needle and the pressure will rapidly drop, thereby signaling entry into the epidural space. Furthermore, pressure readings can be monitored or examined for presence (e.g., right panel) or absence (e.g., left panel) of the characteristic pressure waveform (Step 510). Muscle, which also may exhibit a loss of resistance or pressure change upon needle entry, can be differentiated from the epidural space by the absence or presence of a positive pressure epidural waveform. Upon confirmation of needle positioning in the epidural space, an epidural catheter can be introduced through the needle (Step 512). It is possible that the user could accidently insert the needle too far and enter the CSF space. The CSF space will also show a pressure waveform. To distinguish the epidural space from the CSF space or a vein, the user can aspirate slightly to look for a return of CSF fluid or blood, which would indicate entry of the needle into the CSF space or a vein, respectively (Step 514). The absence of any fluid would indicate that the needle is likely in the epidural space. Thus, epidural space can be distinguished from other tissue (e.g., from CSF space or vein), even in the event of loss of resistance and detection of waveform pressure, e.g., by aspirating fluid for identification of return CSF fluid or blood. The aspiration step may be performed at various stages of the process. With the catheter positioned, anesthesia can be administered to the patient (Step 516).

Figure 7:
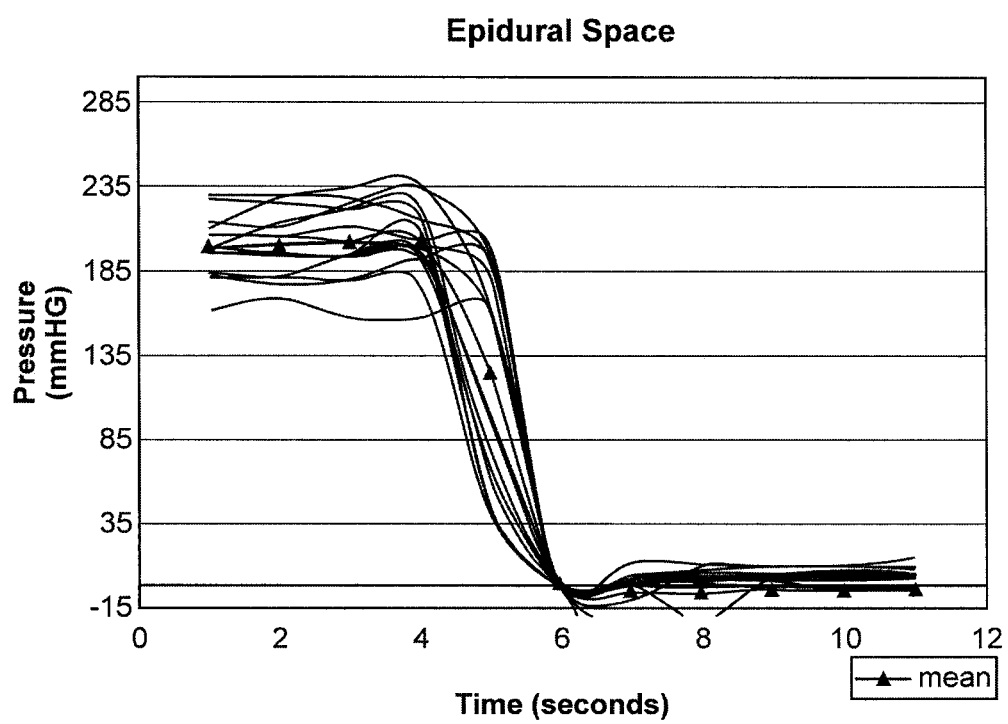
FIG. 7 provides literature pressure vs. time spectra illustrating decreased pressure as progressing into an epidural space.

As indicated, during advancement of an epidural needle a pressure drop can be detected by the device and output to the device display for notification to the user, signaling entry of the needle into the epidural space. FIG. 7 illustrates literature reported exemplary pressure changes as progressing toward and into the epidural space. As is demonstrated in FIG. 7, the saline was pressurized to over 100 mm Hg in the ligament, but the pressure dropped to less than 50 mm Hg within one second after entering the epidural space (as the saline left the end of the needle and entered the epidural space).

Figure 8:
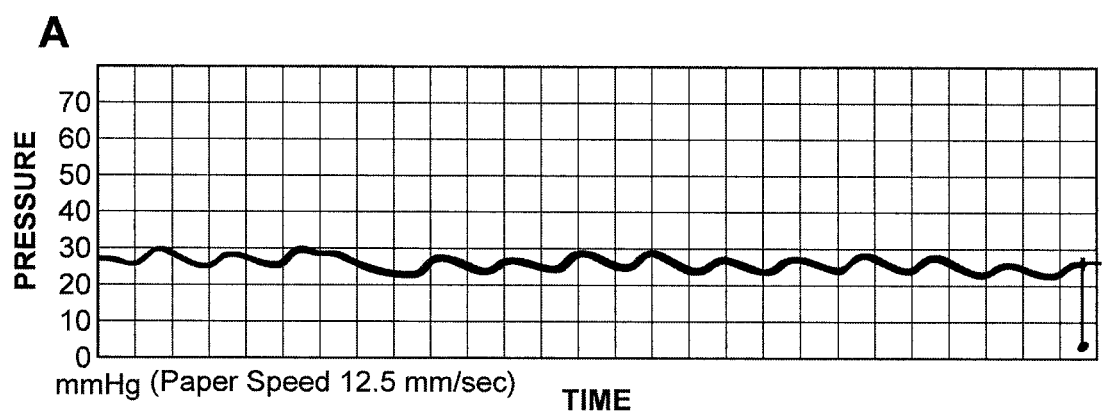
FIG. 8 depicts an exemplary illustration of a detectible pressure waveform pattern from an epidural space.

In addition to the pressure drop, a waveform will then be detectable to the device if the needle is in fact within the epidural space, and detection of a waveform can be output to the user via the device (e.g., device display). FIG. 8 illustrates an exemplary waveform pattern showing pressure data over a period of time. Such waveform pressure data can be output to the device display such that the pressure waveform can be a notification or visualized by the user. Similar to above, the device can include programming or instructions, stored on a computer readable media, for processing pressure data so as to identify a pressure signal/data as epidural waveform, with notification or output to the user selectable from a variety of forms.

In yet another embodiment, a device of the present invention can optionally include a built-in a system for buffering or relieving internal device pressure that may modulate due to a factor(s) other than physiological parameter detection/monitoring. Such pressure modulations may occur, for example, during device handling or positioning, and their registration with the device can interfere with optimal detection or monitoring of the target environment. As such, in some instances a device of the present invention may include a pressure relief or buffer system designed to accommodate pressure changes that might occur due to device handling or positioning, and allow more accurate or optimal detection of pressure within the tissue or target environment.

A pressure relief/buffer system may be selected for a variety of different designs or configurations. In one example, a system may include one or more built in relief valves that allow escape of pressure built up, e.g., from component compression and/or handling of the device. As another illustrative example, a pressure relief/buffer system may include a recalibration or re-zeroing system. For example, pressure buildup may be expected during an initial phase of device positioning, such as initial gripping of the device or insertion into a patient's tissue. Where the device includes a recalibration/re-zeroing system, following initial positioning the device may then be recalibrated, e.g., by re-setting the pressure reading to baseline such that changes in pressure in the patient's tissue are more apparent or more optimally detected/observed.

Figure 9A:
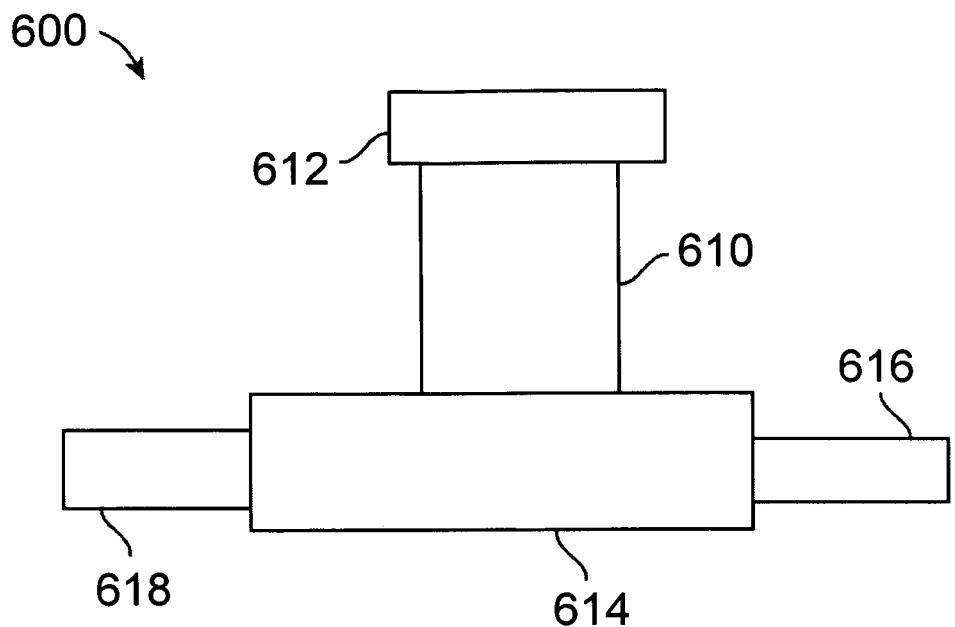
FIG. 9A is a diagram of a device including a pressure relief or pressure buffer system, according to an embodiment of the present invention.
Figure 9B:
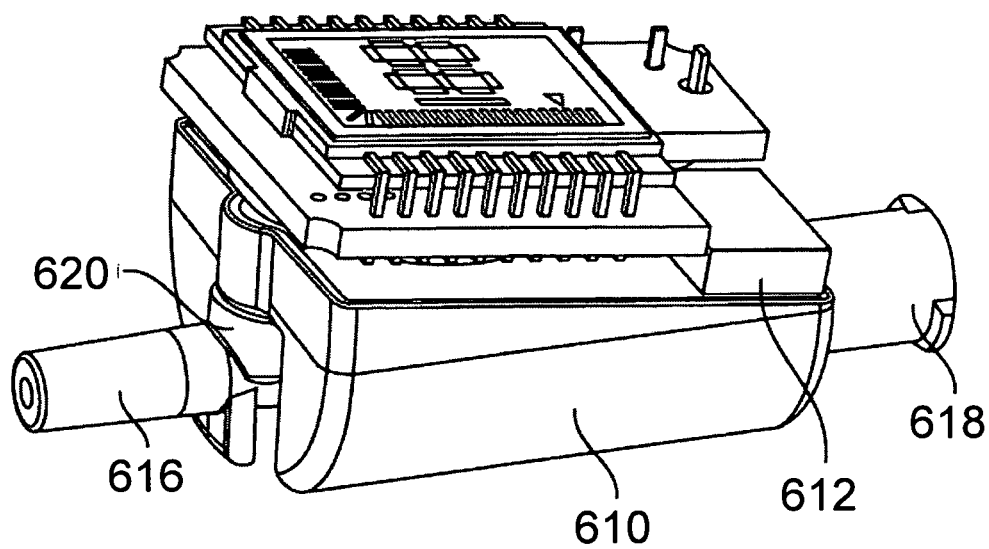
FIG. 9B illustrates a device, having a structure as generally diagrammed in FIG. 16A, including a pressure relief or pressure buffer system, according to an embodiment of the present invention.

In another embodiment, a pressure relief/buffer system of a device can include a reservoir disposed in the device to function as a sort of buffer or capacitor to accommodate small volume fluctuations that result in pressure changes from factors other than tissue/target pressure monitoring. A pressure buffer/relief system of a device 600 including a reservoir 610 disposed between a pressure tube 612 and a fluid channel 614 of the device is illustrated with reference to FIGS. 9A and 9B. The device includes a fluid channel 614 having a distal or front portion 616 that connects to a needle that is inserted into a patient's tissue. The rear or proximal portion 618 of the device includes an opening that can couple to a syringe, but which may be contacted or covered by the user's thumb during certain aspects or periods of device use. The pressure tube 612 couples to a pressure sensor (not shown) of the device. Where the fluid channel 614 is occluded on both ends, air trapped in the fluid channel may become compressed during device handling, such as by contact between the proximal portion 618 opening and the user (e.g., user's hand/finger), with such compressing of air potentially causing increase in pressure within the device. The pressure buffer/relief system permits accommodation of such pressure changes and minimizes interference with monitoring/detection of pressure in the target tissue. The reservoir 610 provides an expanded air volume that minimizes pressure fluctuations registering due to such minor air displacement.

Figure 9C:
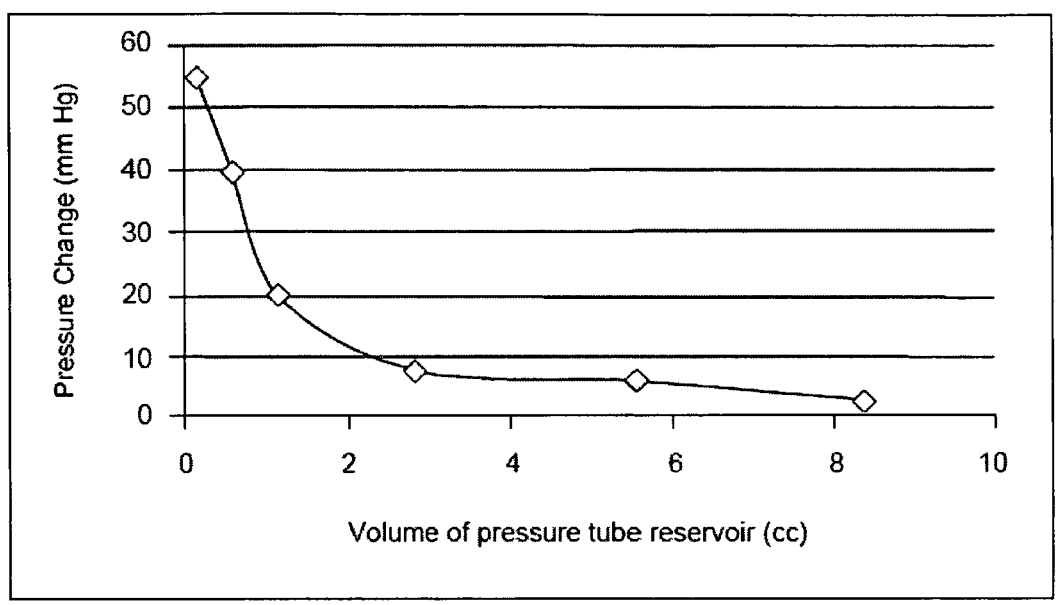
FIG. 9C illustrates pressure changes relative to device reservoir volumes, where pressure changes are due to device handling activities.

In the illustrated embodiment (FIGS. 9A and 9B), for example, a small hole or passage 620 exits off the fluid channel 614 and enters the air reservoir 610. The reservoir 610 can have a volume of about a few cc's to a dozen or more cc's. As any change in pressure is proportional to the relative change in volume ($\Delta P = \Delta V/V$), the added reservoir 610 increases V and subsequently reduces the pressure increased caused by a given compression of the air. Fluid that enters the distal or tissue end 616 of the device passes from the tissue end, through the fluid channel 614, and out the proximal portion 618 without filling the reservoir 610. The volume of a reservoir is proportional to the magnitude of the pressure change accompanying a change in volume (1/V relationship), as illustrated with reference to FIG. 9C, which shows data collected for registered pressure changes due to device handling activities using reservoirs of different volumes.

The device may be designed such that fluids (e.g. blood or cerebrospinal fluid) are not trapped within the device's air reservoir, but rather exit the rear of the device to collect for analysis. In lumbar puncture techniques, for example, the appearance of the CSF at the rear of the device can be used to confirm entry of the needle into the CSF space. Further, such a device design may also expedite how quickly the fluid appears at the rear of the device—if the chamber within the device filled with the CSF, this would delay the appearance of the CSF at the rear of the device and waste precious CSF.

Other relief/buffer systems that may be used instead or in conjunction with the air reservoir system, including those described above. For example, a device may include a cap at the end of the device with a hole reduced in size so as to limit the amount of air that can be compressed by user contact with the proximal end of the device. Further, software algorithms can be utilized which minimize spikes of pressure that may be caused by rapid air compression during device handling or initial positioning. Alternatively, a one way valve at the proximal end may be included that allows fluid to exit the device but does not allow air compressing within the main body of the device due to proximal end contact by the user.

Figure 10:
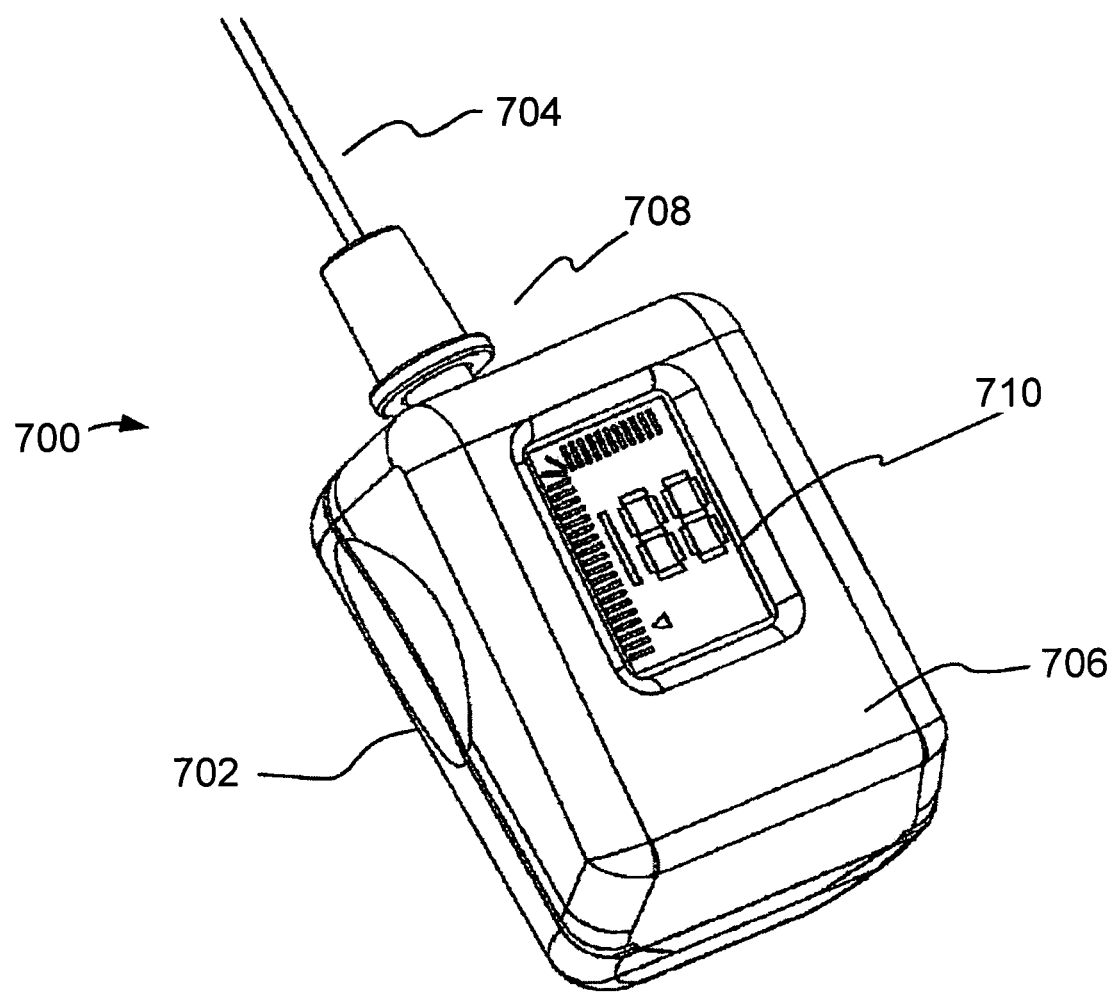
FIG. 10 illustrates an assembly including a detection device with a closed proximal portion and a distal portion coupled to a probe, according to an embodiment of the present invention.

In yet another embodiment, a device of the present invention can include a "closed" portion, such as a closed proximal portion lacking a port. FIG. 10 illustrates an assembly 700 including a detection device 702 coupled with a probe 704. The device 702 includes a housing 706 including a distal portion and a proximal portion. The distal portion of the housing includes a port 708 couplable to the probe 704. The proximal portion of the device 702 is closed in the sense that it lacks a port or opening. Additional components, including those described above such as a sensing unit, processing unit, output unit, etc. (not shown), can be further carried by the housing, with the housing of a device including a single piece or multipiece assembly. The assembly 700 includes an "in-line" configuration with respect to the coupled probe 704 and device 702, similar to as described above. The device 702 further includes a display 710 carried by the housing 706. The display 710 may be disposed on the housing 706 and angled proximally so as to allow more optimal viewing by a user during manipulation of the assembly 700, such as positioning a distal portion of the probe 704 in a tissue of a patient.

In certain embodiments, indicated above, a device of the present invention can be coupled wirelessly to one or more graphical displays positioned remotely from the device, thereby enabling wireless monitoring of signal detection with the device. As an example, the detection device could have both a local display and also transmit data (e.g. pressure data) wirelessly to a remote monitor or device. As another example, the data from the detection device can be transmitted wirelessly to a storage unit, allowing storage and later retrieval of the data. Such storage and retrieval might be utilized, for example, for quality control, diagnostic, or research purposes. For example, the storage unit could save opening pressures during lumbar puncture procedures. A time stamp or the serial number of the particular pressure transducer could assist with identifying the data at a later time. Detection data can be collected and processed, and then utilized to update or reconfigure programming in new and/or existing devices, e.g., for improved performance.

A wireless system could also be used to change display monitors without the need to move additional hardware, such as bulky wires. For instance, a dongle or other type of wireless receiver could receive data from the device and convert the wireless signal to a standard electrical output signal (e.g. 5 V/mm Hg) to impute to a remote monitor. If a patient is transported, the dongle could be moved from a permanent monitor to a portable monitor for transport, and then plugged into a second permanent remote monitor once the patient reaches the new destination. Alternatively, the display on the device could be used during transport, obviating the need for a separate transport monitor. The data could also be directly transmitted to an alternate wireless device, such as a PDA device, without the need for a dongle. Special software could register the disposable pressure sensor to the dongle or device to avoid cross-talk between multiple pressure sensor/wireless receiver units. Alternatively, the dongle and pressure sensor could come together in a disposable pouch and be pre-registered to avoid crosstalk or other type.

The above applications and indications are provided for exemplary purposes. The indications disclosed herein will not be limiting, and the present invention will find use in a variety of additional applications.

Devices can be configured for a single application or for multiple different applications. A device may include a button or switch allow the device algorithm and display to transition from different units of measurements, output configurations, graphical displays and/or one indication to the next. This transition might include scaling the bar graph, changing the display units (mm Hg to cm $H_2O$), changing the display rate, etc. An indicator will alert the user to what mode the device is in. Alternately, the device could automatically change modes by monitoring the pressure readings (e.g. autoscaling the bar graph or changing modes based on the magnitude of the pressure and/or the rate of change in the pressure). For example, a pressure changing from 0 mm Hg to 20 mm Hg at 1 Hz might indicate the CSF space, and a constant pressure of 10 mm Hg might indicate a muscle compartment.

In yet another embodiment, the device can contain alert means, such as indicators (visual or audio) that trigger when certain pressure ranges are encountered, such as pressure ranges anticipated for entry into the spinal canal, or pressure reading patterns (e.g., waveform). The alerts could also activate if the needle or catheter is removed from a pressurized fluid (e.g. a "needle dislodgement" indicator). The device can also have user set alerts and/or the device could have colored LED's (or distinct audio tones) that indicate certain pressure ranges (e.g. yellow for a first pressure range, green for a second range, and red for a third range).

In another embodiment the present invention further provide a kit, which can include one or more detection device components as described herein. A kit may be assembled for portability, as well as use in a medical or surgical setting, and the like. A kit typically includes a detection device of the present invention, and the detection device may be provided in a fully assembled, partially assembled, or non-assembled configuration. As indicated, a device of the present invention may be configured or of a design such that one or more components of the detection device or corresponding assembly have a limited or single use, or are replaceable. As such, a kit can include a detection device with one or more replacement components, such as one or more replacement needles, syringes, etc. In another embodiment, a kit may be designed for a single use only. A kit may include pre-sterilized components or device(s), as well as sterilized packaging.

The components of the present invention may be sterilized (and will generally be sterilizable) by any of the well known sterilization techniques, depending on the type of material. Suitable sterilization techniques include heat sterilization, radiation sterilization, chemical/gas sterilization, and the like.

The specific dimensions of any of the detection devices, systems, and components thereof, of the present invention may vary depending upon the intended application, as may be apparent to those of skill in the art in view of the disclosure herein. For example, selected probe or needle size, design or dimensions will typically differ depending on whether a lumbar puncture or epidural access procedure is intended. For a lumbar puncture, a corresponding lumbar puncture needle will be selected and will generally be sized smaller compared to a needle for an epidural access procedure. A lumbar puncture needle, for example, can generally be sized from about 18 gauge to about 27 gauge. An epidural needle can generally be sized from about 16 gauge to about 20 gauge.

It will be understood that the examples and embodiments described herein are for illustrative purposes and that various modifications or changes in light thereof may be suggested to persons skilled in the art and are included within the spirit and purview of this application and scope of the appended claims. Moreover, different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A method for detecting positioning of a probe in a tissue of a patient having a spinal canal, comprising:
   providing a device comprising a housing having a proximal portion and a distal portion, the distal portion coupled to the probe, the device further comprising:
      a tissue pressure sensing system at least partially carried by the housing and comprising a processing unit coupled with a pressure sensor, the processing unit configured to receive tissue pressure signals comprising a series of instantaneous tissue pressure values from the pressure sensor and determine a mean tissue pressure value over a predetermined period of time with a moving average of the series, the mean tissue pressure value indicative of a tissue environment about a distal portion of the coupled probe; and
      an output unit carried by the housing and comprising a visual display, the output unit coupled to the pressure sensing system so as to receive the mean tissue pressure value signal and output to the visual display the determined mean tissue pressure value, thereby indicating positioning of the probe in the tissue of the patient;
   advancing the output unit and the probe distally such that a distal portion of the probe advances through the tissue of the patient and toward the patient's spinal canal with the mean tissue pressure shown on the visual display; and
   detecting a change in the mean tissue pressure value about the distal portion of the coupled probe during said advancing indicating probe positioning in the patient's spinal canal.

2. The method of claim 1, wherein the probe is rigidly coupled to the device so as to allow positioning of probe by position manipulation of the device housing by a user.

3. The method of claim 1, wherein the probe is directly coupled to the device.

4. The method of claim 1, comprising coupling the probe to the distal portion of the device following insertion of the probe into ligament tissue in the patient's back tissue.

5. The method of claim 1, wherein advancing the device comprises entering the probe into epidural space of the patient's spinal canal.

6. The method of claim 5, further comprising introducing pressure into the device prior to and/or while advancing the probe into the epidural space.

7. The method of claim 6, detecting a decrease in detected mean pressure as indication of entry into the epidural space.

8. The method of claim 5, detecting a pressure waveform indicating positioning of the probe in the epidural space.

9. The method of claim 5, introducing an epidural catheter through the probe following detection of entry into the epidural space.

10. The method of claim 1, wherein advancing the device comprises advancing the probe through dura and entering into the subarachnoid space.

11. The method of claim 10, comprising detecting an increase in pressure as an indication of entry into the subarachnoid (CSF) space.

12. The method of claim 10, comprising detecting a pressure waveform indicating positioning of the probe in the CSF space.

13. The method of claim 10, further comprising flowing fluid into the probe, device or coupled syringe for cerebrospinal fluid (CSF) collection or further indication of probe positioning.

14. The method of claim 10, further comprising monitoring pressure of the CSF during a fluid collection.

15. The method of claim 14, further comprising discontinuing fluid collection in response to detected pressure readings.

16. The method of claim 10, detecting CSF pressure indicative of a pathological condition.

17. A device for detecting positioning of a coupled probe in a tissue of a patient, the device comprising:
a housing having a distal portion with a first port that is detachably couplable to a probe, and a proximal portion, the housing graspable with a hand of a user to advance the housing and the probe toward the tissue;
a tissue pressure sensing system at least partially carried by the housing and comprising a processing unit coupled with a pressure sensor, the processing unit configured to receive tissue pressure signals comprising a series of instantaneous tissue pressure values from the pressure sensor and determine from the received signals a mean tissue pressure value over a predetermined period of time with a moving average of the series, the mean tissue pressure value indicative of a tissue environment about a distal portion of the coupled probe, the predetermined period of time selected such that the mean tissue pressure value is indicative of a position of the distal portion of the coupled probe during positioning in tissue; and
an output unit carried by the housing and comprising a visual display, the output unit coupled to the pressure sensing system so as to receive the mean tissue pressure value and output to the visual display a reporting signal indicating the determined mean tissue pressure value, thereby indicating positioning of the probe in the tissue of the patient.

18. The device of claim 17, further comprising a memory having instructions that when executed cause the processing unit to process one or more signals received from the pressure sensor to determine a change in mean pressure indicative of i) entry into epidural space; ii) entry into CSF space; iii) a pressure waveform characteristic of a patient's spinal canal; or iv) a combination thereof.

19. The device of claim 17, wherein the device is sized for hand-held use by a medical provider.

20. The device of claim 19, the housing comprising a gripping portion with the display carried by the housing on a side generally opposite the gripping portion.

21. The device of claim 19, wherein the visual display is angled proximally relative to a long axis of the devices.

22. The device of claim 17, the proximal portion of the housing comprising a second port that is detachably couplable to a syringe, and the first port fluidly coupled to the second port.

23. The device of claim 22, further comprising a probe coupled to the first port and a syringe coupled to the second port such that the probe, device, and syringe are arranged axially and in sequence.

24. The device of claim 17, the probe comprising an epidural needle or a lumbar puncture needle.

25. The device of claim 17, further comprising a pressure relief or buffer system structured to accommodate non patient-anatomical fluctuations of pressure in the device.

26. The device of claim 25, the pressure relief or buffer system comprising a reservoir disposed between a pressure tube and a fluid channel.

27. The method of claim 5, further comprising aspirating the probe to determine a presence or absence of CSF or blood fluid.

28. A device for detecting positioning of a coupled probe in a tissue of a patient, the device comprising:
a tissue pressure sensing system at least partially carried by a housing and comprising a processing unit coupled with a pressure sensor, the housing graspable with a hand of a user and couplable to a probe having a distal portion, the processing unit configured to receive a plurality of pressure signals comprising a series of instantaneous tissue pressure values from the pressure sensor and determine from the plurality of pressure signals a mean tissue pressure value over a predetermined period of time with a moving average of the series selected such that the mean tissue pressure value is indicative of a position of the distal portion of the coupled probe during positioning in tissue; and
an output unit carried by the housing and comprising a visual display, the output unit coupled to the pressure sensing system so as to receive the mean tissue pressure value and the series of instantaneous tissue pressure values and output to the visual display the determined mean tissue pressure value and the series of instantaneous pressure values, thereby indicating positioning of the probe in the tissue of the patient,
wherein the visual display comprises a readout display carried with the housing for displaying both the determined mean tissue pressure value and the series of instantaneous tissue pressure values in order to position the probe with movement of the housing and the readout display.

29. A device for positioning a probe in tissue of a patient, the device comprising:
a housing comprising a gripping portion and having a distal portion with a first port that is detachably coupleable to a probe such that the probe is rigidly attached to the distal portion, and a proximal portion having a second port fluidly coupled to the first port, wherein the first port and second port are disposed on the housing such that the coupled probe, device and second port are arranged axially and in sequence;
a tissue pressure sensing system at least partially carried by the housing and comprising a processing unit coupled with a pressure sensor to receive a plurality of pressure signals comprising a series of instantaneous pressure values from the pressure sensor and determine from the plurality of pressure values a mean tissue pressure value over a predetermined period of time with a moving average of the series, the mean tissue pressure value indicative of a tissue environment about a distal portion of the rigidly coupled probe, the predetermined period of time being selected such that the mean tissue pressure value is indicative of a position of the distal portion of the coupled probe during positioning in tissue; and an output unit carried by the housing and comprising a visual display carried by the housing, the output unit coupled to the pressure sensing system so as to receive the mean tissue pressure value and output to the visual display the mean tissue pressure value determined with the moving average of the series, thereby indicating positioning of the probe in the tissue of the patient.

30. The device of claim 29, wherein:

the proximal portion of the housing comprising a second port that is detachably couplable to a syringe; and the first port is fluidly coupled to the second port.

31. The device of claim 30, further comprising a probe coupled to the first port and a syringe coupled to the second port such that the probe, device, and syringe are arranged axially and in sequence.

32. The device of claim 29, wherein the reporting signal is continuously updated in real time or near real time.

33. The device of claim 29, wherein the mean pressure value is determined by averaging a series of instantaneous pressure values sensed by the pressure sensor.

34. The method of claim 1, wherein said detecting a change in mean pressure includes detecting a mean anatomical pressure about the distal portion of the coupled probe.

* * * * *